United States Patent
Cohen et al.

(10) Patent No.: US 10,415,035 B2
(45) Date of Patent: Sep. 17, 2019

(54) ANIONIC POLYPLEXES FOR USE IN THE DELIVERY OF NUCLEIC ACIDS

(71) Applicant: B.G. Negev Technologies and Applications LTD, Beer Sheva (IL)

(72) Inventors: Smadar Cohen, Beer Sheva (IL); Olga Kryukov, Beer Sheva (IL); Emil Ruvinov, Arad (IL); Efrat Forti, Omer (IL); Stav Shamir, Eilat (IL)

(73) Assignee: B.G. Negev Technologies and Applications Ltd., Beer Sheva (IL)

( * ) Notice: Subject to any disclaimer, the term of this patent is extended or adjusted under 35 U.S.C. 154(b) by 0 days.

(21) Appl. No.: 15/241,342

(22) Filed: Aug. 19, 2016

(65) Prior Publication Data

US 2016/0354474 A1    Dec. 8, 2016

Related U.S. Application Data

(63) Continuation-in-part of application No. PCT/IL2015/050196, filed on Feb. 19, 2015.

(60) Provisional application No. 61/942,196, filed on Feb. 20, 2014.

(51) Int. Cl.
| | |
|---|---|
| *A61K 47/48* | (2006.01) |
| *C12N 15/113* | (2010.01) |
| *A61K 47/61* | (2017.01) |
| *A61K 31/7105* | (2006.01) |
| *A61K 31/713* | (2006.01) |

(52) U.S. Cl.
CPC .......... *C12N 15/113* (2013.01); *A61K 31/713* (2013.01); *A61K 31/7105* (2013.01); *A61K 47/61* (2017.08); *C12N 2310/14* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 8,722,646 B2 | 5/2014 | Hsu et al. | |
| 2010/0143484 A1* | 6/2010 | Beco Pinto Reis .. | A61K 9/5073 424/491 |
| 2011/0060123 A1 | 3/2011 | Kataoka et al. | |
| 2013/0115699 A1 | 5/2013 | Grayson et al. | |

FOREIGN PATENT DOCUMENTS

| | | | |
|---|---|---|---|
| WO | 2008/131129 A2 | 10/2008 | |
| WO | 2009/039189 A2 | 3/2009 | |

OTHER PUBLICATIONS

Jones, C.H et al; "Overcoming Nonviral Gene Delivery Barriers: Perspective and Future". Molecular pharmaceutic, 10 (11), pp. 4082-4098. (2013).
Shim, M.S. et al: "Stimuli-responsive polymers and nanomaterials for gene delivery and imaging applications". Adv Drug Deliv Rev 64, pp. 1046-1059. (2012).
Krebs et al.; "Localized and Sustained Delivery of Silencing RNA from Macroscopic Biopolymer Hydrogels" Journal of the American Chemical Society 131.26:pp. 9204-9206. (2009).
Amiji et al; "Calcium alginate microparticles as a non-condensing DNA delivery and transfection system for macrophages" Pharmaceutical Engineering pp. 1-8.(2012).
Kapoor et al; "Physicochemical characterization of anionic lipid-based ternary siRNA complexes" Biochimica et Biophysica Acta 1818 pp. 1603-1612. (2012).
Emil Ruvinov et al; "Calcium-siRNA nanocomplexes: What reversibility is all about" Journal of Controlled Release 203 pp. 150-160. (2015).
International Search Report and Written Opinion, dated Jun. 21, 2015, received in connection with International Patent Application No. PCT/IL2015/050196.
Mamta Kapoor et al; "Efficient and safe delivery of siRNA using anionic lipids: Formulation optimization studies" International Journal of Pharmaceutics 432 pp. 80-90. (2012).
Zhao et al; "Alginate modified nanostructured calcium carbonate with enhanced delivery efficiency for gene and drug delivery" Mol Biosyst. 28(3)pp. 753-759. (2012).
Aynié et al; "Spongelike alginate nanoparticles as a new potential system for the delivery of antisense oligonucleotides" Antisense Nucleic Acid Drug Dev.9(3)pp. 301-312. (1999).
Sokolova et al; "Synthesis and characterization of DNA-functionalized calcium phosphate nanoparticles" Materialwissenschaft and Werkstofftechnik vol. 37, Issue 6 pp. 441-445. (2006).
Extended European Search Report issued in EP Application No. 15751868.9, dated Aug. 30, 2017.
Sabrina Oliveira et al; "Targeted Delivery of siRNA" Journal of Biomedicine and Biotechnology, vol. 2006, Article ID 63675, pp. 1-9. (2006).

\* cited by examiner

*Primary Examiner* — James D Schultz
(74) *Attorney, Agent, or Firm* — UltimatEdge IP Law Group, P.C.; Dean G. Stathakis

(57) ABSTRACT

The present invention provides an anionic polyplex formed from a nucleic acid and an anionic polymer and further comprising a cation, which can be in the form of a nanoparticle or a microparticle and compositions comprising the anionic polyplex. The present invention further provides uses of the anionic polyplex such as delivery of the nucleic acid into cells and methods of treating a disease, disorder or condition selected from the group consisting of cancer, a metabolic, a neurodegenerative, a cardiovascular, and an infectious or inflammatory disease or disorder. The present invention also provides an anionic complex comprising a divalent cation and a nucleic acid but lacking an anionic polymer, in the form of a nanoparticle that is capable of forming a colloidal suspension.

11 Claims, 26 Drawing Sheets
Specification includes a Sequence Listing.

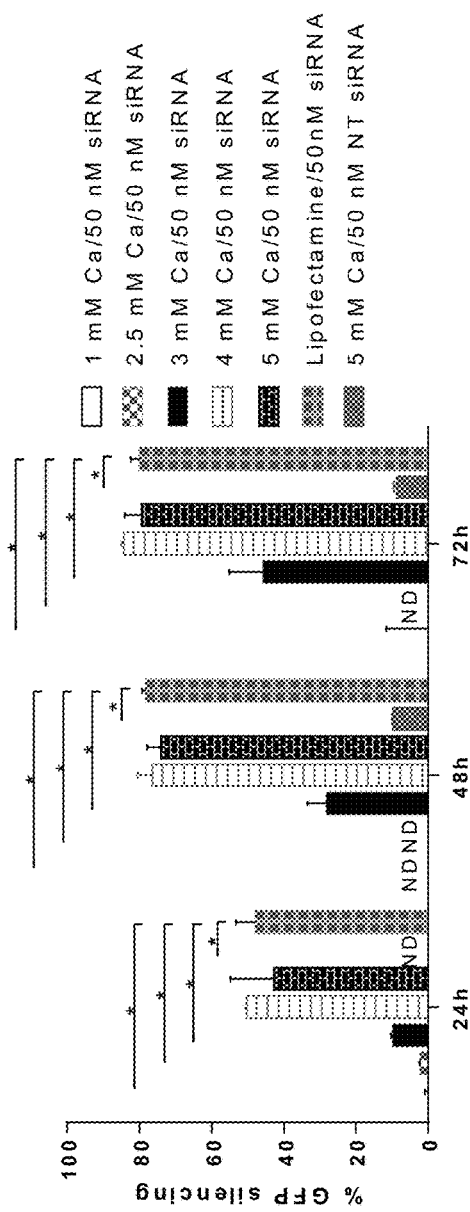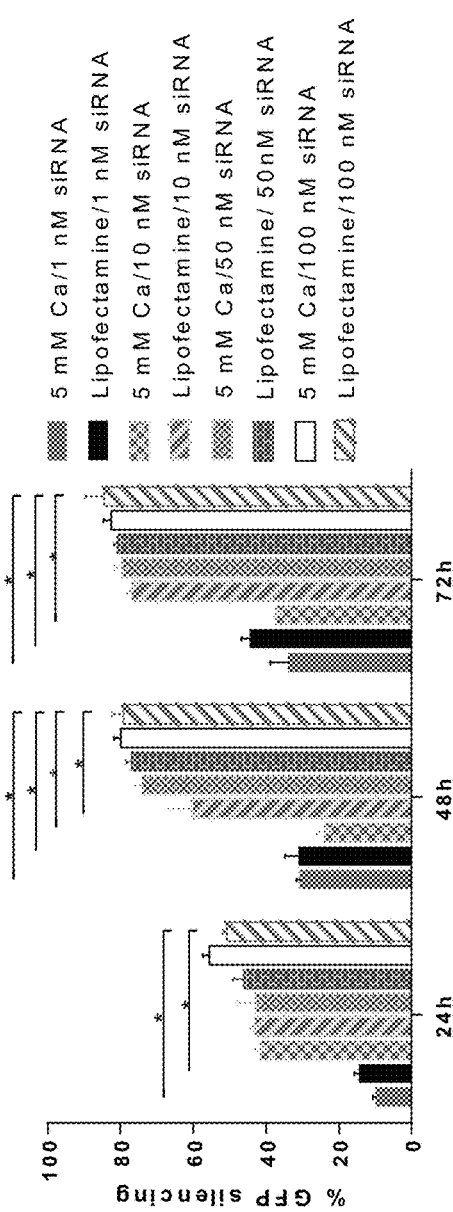

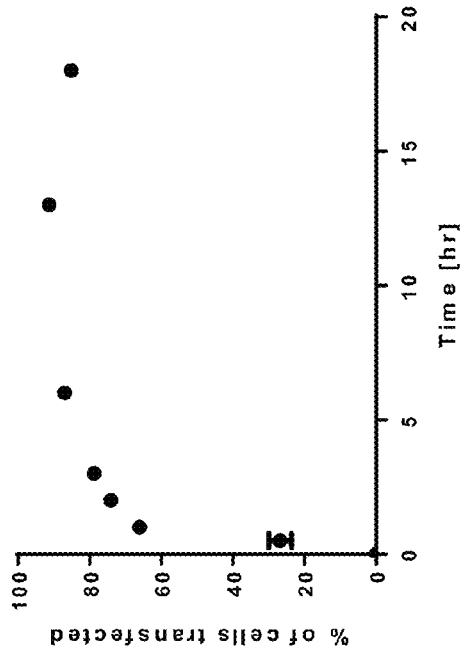
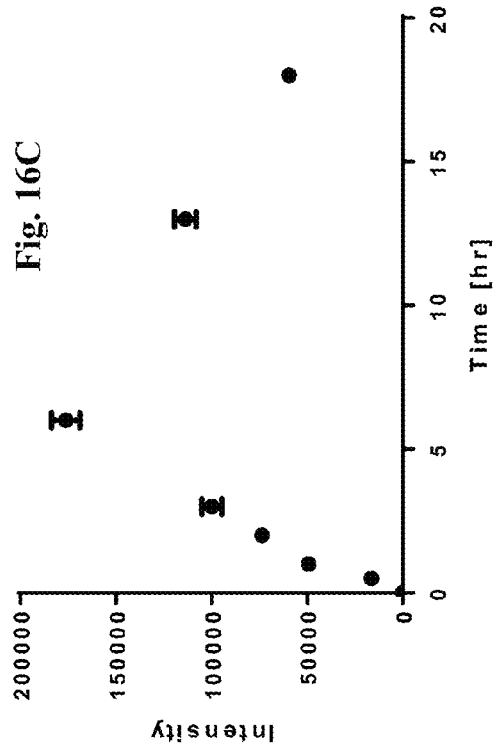
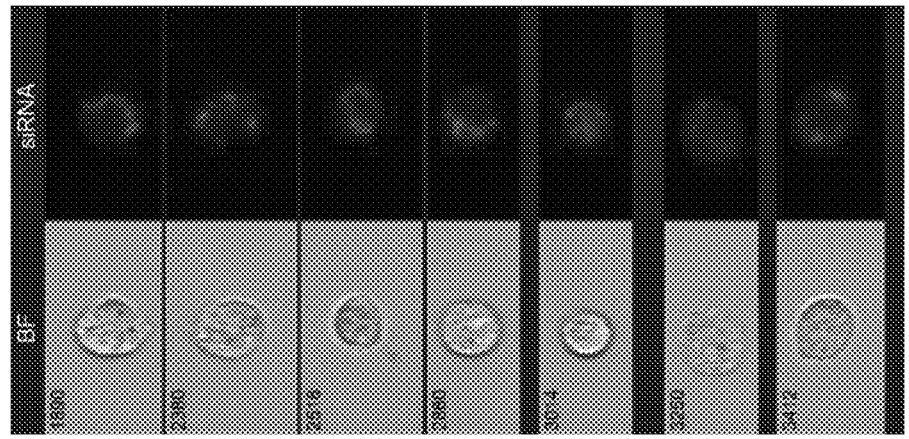

ANIONIC POLYPLEXES FOR USE IN THE DELIVERY OF NUCLEIC ACIDS

CROSS REFERENCE TO RELATED APPLICATIONS

This application is a continuation-in-part of International Application PCT/IL2015/050196 filed Feb. 19, 2015, which claims the benefit of U.S. Provisional Patent Application Ser. No. 61/942,196 filed Feb. 20, 2014, the disclosures of which are expressly incorporated herein by reference.

REFERENCE TO SEQUENCE LISTING

The present application is being filed along with a Sequence Listing in electronic format. The Sequence Listing is provided as a file entitled "10777-003US1_2016_08_19_Sequence_Listing.txt", created Feb. 20, 2014, which is 3.63 Kb in size. The information in the electronic format of the Sequence Listing is incorporated herein by reference in its entirety.

FIELD OF THE INVENTION

The present invention relates to delivery of nucleic acids, particularly DNA and RNA.

BACKGROUND OF THE INVENTION

Nucleic acid materials can be used for the therapeutic modulation of gene expression in the form of small interference RNA (siRNA), antisense RNA, and decoy oligodeoxynucleotides (ODN), as well as for the replacement of defective or missing genes by the expression of exogenously introduced genes. However, most nucleic acid therapeutics have not been shown to be applicable for systemic application due to their very short half-life in the bloodstream and inability to cross cell membranes. Because the delivery of nucleic acid therapeutics to disseminated and widespread disease sites such as metastasized tumors and inflamed tissues can only be achieved by systemic administration, the development of efficient delivery systems suitable for systemic application is crucial to the success of nucleic acid-based therapies (Jones et al., 2013; Shim and Kwon, 2012).

A wide variety of methods has been used to facilitate the delivery of nucleic acids to cells in culture or to whole organism, from cationic chemical agents (cationic lipids, liposomes, polymers or peptides) to physical methods (electrotransfer). Cationic lipid and polymer formulations protect the nucleic acid therapeutics against enzymatic degradation as well as facilitate cellular uptake but may cause severe cytotoxicity and/or serum inactivation probably due to their cationic charge (Kedmi et al., 2010).

SUMMARY OF THE INVENTION

It has been found in accordance with the present invention, that anionic polymers are capable of functioning as carriers for the delivery of nucleic acids into cells by forming polyplexes with the nucleic acid via electrostatic interactions with calcium ions.

Thus, in one aspect, the invention is directed to an anionic polyplex in the form of a nanoparticle or a microparticle formed from a nucleic acid and an anionic polymer and further comprising a cation, wherein said anionic polyplex has a diameter of 50-200 nm.

The invention is also directed to a pharmaceutical composition comprising the anionic polyplex of described above and a pharmaceutically acceptable carrier.

According to another aspect, the invention is directed to the anionic polyplex described above, for use in the delivery of the nucleic acid into cells.

According to still another aspect, the invention is directed to the anionic polyplex described above, for use in the treatment of a disease, disorders or condition selected from the group consisting of cancer, a metabolic, a neurodegenerative, a cardiovascular, an infectious and an inflammatory disease or disorder.

According to an additional aspect, the invention is directed to a method of treating a disease, disorder or condition selected from the group consisting of cancer, a metabolic, a neurodegenerative, a cardiovascular, and an infectious or inflammatory diseases or disorder, comprising administering the anionic polyplex or the pharmaceutical composition described above to a subject in need thereof.

According to yet another aspect, the invention is directed to a method for the preparation of the anionic polyplex described above, mixing said nucleic acid with a salt of a divalent cation that is a strong electrolyte in zwitterionic buffer at physiological pH, and adding said anionic polymer.

According to a further aspect, the invention is directed to a method for stabilizing a nucleic acid, comprising complexing said nucleic acid with an anionic polymer and a cation, thereby stabilizing said nucleic acid.

In yet additional aspects, the present invention provides a stable anionic complex comprising a calcium cation and a nucleic acid but lacking an anionic polymer, wherein said stable anionic complex is in the form of a nanoparticle and capable of forming a colloidal suspension, and methods for producing said complex comprising mixing said nucleic acid with a salt of a divalent cation that is a strong electrolyte in zwitterionic buffer at physiological pH.

BRIEF DESCRIPTION OF DRAWINGS

FIGS. 11A-11B show silencing efficiency of $Ca^{2+}$-siRNA complexes in eGFP-CT26 cells, at indicated time-points post-transfection, evaluated by FACS. A. Silencing efficiency at 50 nM siRNA and various calcium ion concentrations. p (interaction, 2-way ANOVA)<0.0001. *p<0.05 (Dunnett's multiple comparisons test), ND—not detectable. In each time group (from left): 1 mM $Ca^{2+}$ (white); 2.5 mM $Ca^{2+}$ (checkered); 3 mM $Ca^{2+}$ (black); 4 mM $Ca^{2+}$ (striped); 5 mM $Ca^{2+}$ (brick); 5 mM $Ca^{2+}$/NT (non-targeting) siRNA (small checkered); Lipofectamine (ladder); B. Silencing efficiency at 5 mM $Ca^{2+}$ (or Lipofectamine instead, where indicated) and various siRNA concentrations. p (interaction, 2-way ANOVA)<0.0001. *p<0.05 (Dunnett's multiple comparisons test). In each time group (from left): 1 nM siRNA (gray); Lipofectamine/1 nM siRNA (black); 10 nM siRNA (large checkered); Lipofectamine/10 nM siRNA (hatched gray); 50 nM siRNA (small checkered); Lipofectamine/50 nM siRNA (brick); 100 nM siRNA (white); Lipofectamine/100 nM siRNA (hatched white).

FIGS. 16A-16C show uptake of $Ca^{2+}$-siRNA binary complexes by CT26 eGFP cells using ImagstreamX. A. Images showing bright field and siRNA-Cy5 (red) accumulation in representative cells 3 hours post transfection. B. % of cells accumulating siRNA over time, showing saturation at 6 hours. C. Mean fluorescence intensity (MFI) of Cy5 siRNA in transfected cells over time showing a peak after 6 hours.

DETAILED DESCRIPTION OF THE INVENTION

Figure 1A:
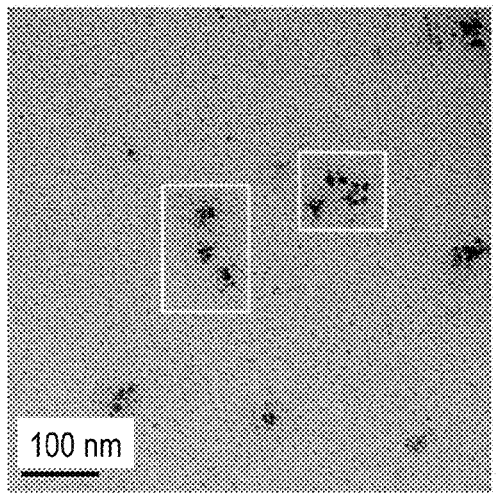
FIGS. 1A-1D show transmission electron microscopy complexes including hyaluronan sulfate (HA-S), $Ca^{+2}$ and siRNA. A-B. Dry-TEM of the complexes (2.5 µM HA-S/250 mM $Ca^{2+}$/250 nM siRNA) with either gold-labeled siRNA (A) or gold-labeled HA-S (B). C-D. Cryo-TEM of the complexes (25 µM HA-S/250 mM $Ca^{2+}$/2.5 µM siRNA) with either gold-labeled siRNA (C) or gold-labeled HA-S (D). White boxes enclose several complexes for convenience.
Figure 1B:
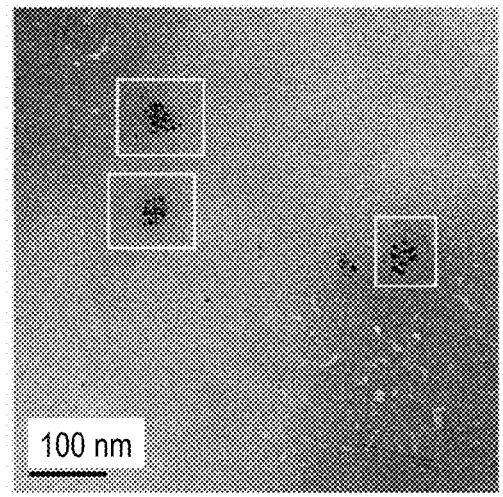

The inventors of the present invention developed anionic carriers for the delivery of nucleic acid therapeutics. In the experiments demonstrated in the present application, polyplexes (also referred to herein as "complexes" or "nucleic acid complexes") are formed from the anionic polymeric carriers and the nucleic acid therapeutics, and the interaction between the nucleic acid therapeutics and the anionic polymer carriers is mediated by electrostatic interactions with calcium ions.

Anionic polymers according to the invention are natural or synthetic polymers which have a net negative charge at physiological pH, i.e. between pH of 7.2 and 7.5, more specifically between pH of 7.3 and 7.4. An anionic polymer according to the invention is selected from the group consisting of an anionic natural polysaccharide or a derivative thereof, and an anionic synthetic polymer. Anionic natural polysaccharides according to the invention include (but are not limited to) hyaluronan (HA), alginate (Alg) and their derivatives such as HA-sulfate (HA-S) and Alg-sulfate (Alg- S), exemplified in the present application. Synthetic anionic polymers including polyesters such as poly(lactic-co-glycolic acid), poly(lactic acid) or polycaprolactone; poly(amino acids) such as poly(glutamic acid); poly(anhydride)s; poly(sodium styrene sulfonates); poly(acrylate)s; and poly(phosphazene)s. Additional anionic polymers that can be used with the invention include anionic proteins.

In some embodiments, the anionic polymer is selected from the group consisting of hyaluronan (HA), alginate (Alg), HA-sulfate (HA-S) and Alg-sulfate (Alg-S).

In some embodiments, the molecular weight of the HA, HA-S, Alg or Alg-S is between 30 and 200 kDa.

Some anionic polymers have inherent biological activity or specificity in the human body and this can enhance their targeting and uptake by certain cells, for example, hyaluronic acid and its sulfated form, HA-S. Hyaluronic acid receptors play important biological roles in endocytosis and signal transduction. Cluster determinant 44 (CD44), receptor for hyaluronic acid-mediated motility (RHAMM), and lymphatic vessel endothelial hyaluronan receptor-1 (LYVE-1) have been identified as hyaluronic acid receptors for various biological functions.

By contrast, alginate and Alg-S are plant-derived anionic polymers which do not have biological specificity in the human body and thus can be used as blank canvas on which specific groups, which are recognized in the human body, can be conjugated, or modified.

Additionally, the anionic polymers of the invention carry inherent functional carboxylates, so that various targeting moieties (peptides, antibodies, receptors) can be attached to their surface, for the purpose of targeting the polyplexes to their target cells (cancer cells, metastases, cells of the immune systems, etc).

Therefore, the anionic polyplex of the present invention may comprise a targeting moiety, such as a ligand. Examples for ligands that can be used for targeting of the polyplex of the present invention to cells or tissues of interest include, for example peptides containing RGD (Arginine-Glycine-Aspartic acid) sequence for binding to specific integrin receptors, growth factor receptors ligands such as EGF and TGFα, or antibodies to tumor-associated antigens.

In addition to their proven biocompability, the anionic polymeric carriers—nucleic acid polyplexes of the invention have additional advantages; the simple preparation method at aqueous conditions ("green technology") is important for mass production of these carriers.

The term "polyplex" as used herein refers to a complex of a polymer and a nucleic acid such as DNA or RNA formed via electrostatic interactions with cations. In cases where the polyplex comprises siRNA, it may be also referred to as "siRNA complex".

In view of the above, in one aspect, the present invention provides an anionic polyplex in the form of a nanoparticle or a microparticle formed from a nucleic acid and an anionic polymer and further comprising a cation, wherein said anionic polyplex has a diameter of 50-200 nm. It follows that said anionic polyplex of the invention comprises the anionic polymer, nucleic acid and cation.

The cation forming part of the polyplex may be a divalent cation or a multivalent cation. For example, the cation may be a divalent cation, such as $Ca^{2+}$, $Ba^{2+}$, $Mg^{2+}$, $Mn^{2+}$, $Cu^{2+}$, $Ni^{2+}$, $Zn^{2+}$ or $Fe^{2+}$; or the cation may be a multivalent cation, such as $Fe^{3+}$, $Mn^{3+}$ or $Mn^{4+}$. The cation functions as an ion bridge between the negatively charged nucleic acid and the negatively charged anionic polymer to form the polyplex, i.e. the complexing between the nucleic acid and the anionic polymer is mediated by electrostatic interactions with the cations. The interaction with the cation may be in the form of a cation bridge. In particular, the divalent cation is $Ca^{2+}$, and the polyplexing between the nucleic acid and the anionic polymer is mediated by electrostatic interactions with calcium ions. In certain polyplexes of the present invention, the cation forming part of the polyplex is not multivalent. In certain embodiments the calcium cation is not in the form of calcium phosphate. In certain embodiments, the cation is provided as a salt that is a strong electrolyte, i.e. it is substantially dissociated in aqueous solution. For example, the electrolyte may have a degree of dissociation that is close to 1.

Because of the electrostatic interactions between the cations, the negatively charged nucleic acid and the negatively charged anionic polymer, a positively charge polymer is not needed.

Therefore, in some embodiments, the polyplex of the invention does not comprise a positively charged polymer.

The nucleic acid being part of the polyplex described above may be selected from the group consisting of DNA, such as a plasmid DNA (pDNA), an oligodeoxynucleotide (ODN), and RNA such as siRNA, mRNA or miRNA. In some embodiments, the nucleic acid is siRNA.

According to some embodiments, the anionic polyplex of the invention is selected from the group consisting of an (alginate)-$Ca^{2+}$-siRNA polyplex, an (alginate-sulfate)-$Ca^{2+}$-siRNA polyplex, a (hyaluronan)-$Ca^{2+}$-siRNA polyplex and a (hyaluronan-sulfate)-$Ca^{2+}$-siRNA polyplex.

The molar ratio of anionic polymer to RNA may vary depending on the molecular weight of the anionic polymer, and may be between 100:1 and 0.01:1, between 50:1 and 0.01:1, between 20:1 and 0.01:1, between 18:1 and 0.01:1, between 16:1 and 0.01:1, between 14:1 and 0.01:1, between 12:1 and 0.01:1, between 10:1 and 0.01:1, between 8:1 and 0.01:1, between 6:1 and 0.01:1, between 4:1 and 0.01:1, or between 2:1 and 0.01:1, between 10:1 and 0.05:1, between 5:1 and 0.05:1, between 3:1 and 0.05:1, between 1:1 and 0.05:1, between 10:1 and 1:1, between 5:1 and 1:1, or between 3:1 and 1:1, or said ratio of anionic polymer to RNA or of RNA to anionic polymer is 100:1, 50:1, 20:1, 18:1, 16:1, 14:1, 12:1, 10:1, 8:1, 6:1, 4:1, 2.5:1, 2:1, 1:1, 0.8:1, 0.4:1, 0.25:1, 0.1:1 or 0.08:1.

In some embodiments, the anionic polymer is HA-S and the ratio of HA-S to RNA is about 10:1 or about 1:1. In some embodiments, the ration of HA-S to RNA is about 1:1.

In some embodiments, the anionic polymer Alg-S and the ratio of Alg-S to RNA is about 6:1.

The molar ratio of anionic polymer to DNA or DNA to anionic polymer may vary depending on the molecular weight of the anionic polymer, and may be between 10000:1 to 1:1, between 8000:1 to 1:1, between 6000:1 to 1:1; between 5000:1, between 4000:1 to 1:1 to 1:1, between 3000:1 to 1:1, between 2000:1 to 1:1, between 1000:1 to 1:1, between 800:1 to 1:1, between 600:1 to 1:1, between 400:1 to 1:1, between 200:1 to 1:1, between 100:1 to 1:1, between 50:1 to 1:1, between 25:1 to 1:1, between 20:1 to 1:1, between 18:1 and 1:1, between 16:1 and 1:1, between 14:1 and 1:1, between 12:1 and 1:1, between 10:1 and 1:1, between 8:1 and 1:1, between 6:1 and 1:1, between 4:1 and 1:1, or between 2:1 and 1:1 or said ratio of anionic polymer to DNA is about 3000:1.

In some embodiments, the zeta potential, or surface charge of the anionic polyplexes is more negative than −5 mV.

The final concentration of $Ca^{2+}$ may vary between 0.5-10 mM, in particular above 3 mM, depending, inter alia, on the cell type targeted for introduction of the polyplexes. In some embodiments, the final concentration of $Ca^{2+}$ is about 5 mM.

The term "about" as used herein, means that values that are 10% or less above or below the indicated values are also included.

It has been found in accordance with the present invention that polyplexes comprising hyaluronic acid or alginate or sulfated derivatives thereof efficiently introduce the nucleic acid into cells, be it RNA or DNA. Once inside the cell, certain nucleic acids, such as siRNA are capable of specifically silencing certain target genes by reducing the level of mRNA transcribed from these genes, which, in turn, can affect the expression of downstream genes (see Example 8). In the case of plasmid DNA, genes encoded thereon are efficiently expressed and their expression can result in up- or down-regulation of downstream genes.

As described in Example 8 (and FIG. 9), polyplexes of HA-S and siRNA can be used to modulate expression of genes downstream from the target gene. In this example, (HA-S)-Ca-siSTAT3 polyplexes were successful in reducing the expression of the acute phase response genes serum amyloid A1 (SAA1) and fibrinogen, which had been induced by IL-6 in HepG2 cells.

Thus, the polyplex of the present invention may be used in the delivery of a nucleic acid to cells. Additionally, the polyplex of the present invention may be used in order to silence or modulate the expression of genes in the cells to which the nucleic acids are delivered.

In some embodiments, the nucleic acid is capable of silencing of a gene associated with a disease, disorder or condition selected from the group consisting of cancer, a metabolic, a neurodegenerative, a cardiovascular, and an infectious or inflammatory disease or disorder. In some embodiments, the siRNA is for silencing of the gene STAT3.

All of the relevant features and embodiments described above in the context of the first aspect also apply to each of the aspects described below.

In another aspect, the present invention provides a pharmaceutical composition comprising the polyplex of the present invention as defined hereinabove and a pharmaceutically acceptable carrier.

Pharmaceutical compositions for use in accordance with the present invention may be formulated in a conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for oral administration.

The term "carrier" in the context of a pharmaceutical composition refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In a further aspect, the present invention is directed to an anionic polyplex for use in the delivery of a nucleic acid to cells. For this purpose, the anionic polymer may be in a complex with a cation and the nucleic acid to be delivered to the cells. The nature of the anionic polymer and the cation of this aspect are as defined above in the context of the polyplex.

In still another aspect, the present invention provides a kit for use in delivery of a nucleic acid to cells, said kit including a first container comprising an anionic polymer as defined above, a second container comprising a cation as defined above, a third container comprising a desired nucleic acid for delivery into cells, and a leaflet with instructions for mixing said ingredients.

The cells, to which the nucleic acid is delivered according to any one of the different aspects of the present invention, may be selected from the group consisting of cells in culture, either adherent to a substrate or in suspension, and cells in a living tissue such as solid tissue and blood, i.e., cells that are part of a living organism. These cells may be diseased cells, such as cancer cells, and therefore, the anionic polyplex of the present invention may be useful in gene therapy, for example, wherein the gene therapy comprises controlling the expression level of a gene. The cells can further be selected from various types of cells, such as immune cells, skin cells, stem cells, nerve cells, muscle cells or endothelial cells. The gene therapy may control the expression level by decreasing it or increasing it. The gene therapy may be used to treat diseases, disorders or conditions that are amenable to intervention by decreasing or increasing the expression of certain genes, the aberrant expression of which causes, or is associated with, the diseases, disorders or conditions.

Thus, the anionic polyplex of the present invention may be used in the treatment of diseases, disorders or conditions selected from the group consisting of cancer, a metabolic, a neurodegenerative, a cardiovascular, and an infectious or inflammatory disease or disorder. The present invention further contemplates the use of each one of its different aspects for controlling cell behavior and fate, pluripotency, differentiation, morphology, etc.

In an additional aspect, the present invention provides a method for treatment of a diseases, disorder or condition in a subject in need thereof, comprising administering to said subject an anionic polyplex or the pharmaceutical composition as defined herein above. The disease or disorder can be selected from the group consisting of cancer, a metabolic, a neurodegenerative, a cardiovascular, and an infectious or inflammatory disease or disorder.

The term "treating" or "treatment" as used herein refers to means of obtaining a desired physiological effect. The effect may be therapeutic in terms of partially or completely curing a disease and/or symptoms attributed to the disease. The term refers to inhibiting the disease, i.e. arresting its development; or ameliorating the disease, i.e. causing regression of the disease.

According to a further aspect, the present application provides a method for the preparation of the anionic polyplex of the present invention, comprising mixing said nucleic acid with a salt of a divalent cation that is a strong electrolyte in zwitterionic buffer at physiological pH, and adding said anionic polymer.

It has been found in accordance with the present invention that the polyplex of the present invention is protected against degradation by a nuclease, i.e. the nucleic acid is stabilized when complexed via the cation to the anionic polymer. As an example, it was shown that siRNA is protected against degradation by RNase A.

Thus, in yet an additional aspect, the present invention is directed to a method for stabilizing a nucleic acid, comprising mixing said nucleic acid with a salt of a divalent cation that is a strong electrolyte in zwitterionic buffer at physiological pH, and adding said anionic polymer, thereby stabilizing said nucleic acid.

In certain embodiments, the divalent cation is selected from the group consisting of $Ca^{2+}$, $Ba^{2+}$, $Mg^{2+}$ and $Mn^{2+}$, in particular $Ca^{2+}$. In certain independent embodiments, the salt is $CaCl_2$, the zwitterionic buffer is HEPES, and the nucleic acid is siRNA.

Examples of zwitterionic buffer, also known as Good buffers, appropriate for keeping a physiological pH and for use in accordance with the methods of the present invention are well known to the person skilled in the art according to their accepted acronym or common name: MES, ADA, PIPES, ACES, MOPSO, Cholamine Chloride, MOPS, BES, TES, HEPES, DIPSO. Acetamidoglycine, TAPSO, POPSO, HEPPSO, HEPPS, Tricine, Glycinamide, Bicine, TAPS, AMPSO, CABS, CHES, CAPS and CAPSO.

The present inventors show that, at the conditions used in the experiments of Example 2 below, the polyplexes of the present invention form almost spherical nano-sized structures. Thus, the present invention further contemplates nano- or micro-particles comprising an anionic polymer, a cation and a nucleic acid as defined above. The present invention also provides an anionic polyplex as described above, in the form of a nanoparticle or a microparticle. In certain embodiments, the diameter of the nanoparticle is in the range of 50-200 nm.

The present inventors have further found that also a binary anionic complex lacking an anionic polymer, which comprises a complex of siRNA and calcium, is stable, capable of entering cells and releasing the siRNA there, and silencing the targeted gene (see Examples 10-13). In contrast to the ternary anionic polyplex of the present invention, this simpler type of nucleic acid complex is not amenable to the addition of targeting moieties. The inventors found that, in contrast with complexes formed with calcium phosphate (a weak electrolyte) that results in uncontrollable growth of calcium phosphate crystals in physiological solutions that could result in significant cytotoxicity, the binary complex formed with $CaCl_2$ (a salt that is a strong electrolyte with close to complete dissociation of the ions in water), forms nanoparticles and a colloid suspension when mixed with an aqueous solution. In certain embodiments, the size of the nanoparticles is in the range of 50 to 100 nm.

The publication of Ruvinov et al. 2015 (J. Controlled Release 203:150-160), which is incorporated by reference herein, further describes calcium-siRNA binary complexes and their features. According to Section 3.2 and FIG. 2B on the same page, complexes of 5 mM calcium: 50 nM siRNA were stable over time. Cytocompatibility was assessed by cell viability (Section 3.3 on page 154 and FIG. 4) and complexes with 5 mM calcium were found to be cytocompatible with no negative impact on cell viability. Section 3.4 shows effective gene silencing by calcium siRNA complexes (FIGS. 5 and 6) as presented in the present invention, Section 3.5 shows cellular uptake of the complexes (FIG. 7).

The term "stable" as used herein with reference to the complexes of the invention, means that these complexes maintain their size, surface charge and composition in physiological conditions and during storage. Example 10 shows stability of the complexes over 24 hours, and Section 3.2 and FIGS. 2B-2C of Ruvinov et al., which are incorporated herein by reference, demonstrate no significant change in size or surface charge of the complexes in 96 hours. According to Section 3.2 on page 153, right column of Ruvinov: "Complexes of 5 mM $Ca^{2+}$:50 nM siRNA were stable over time (FIGS. 2B, C, and Supplementary FIG. S3). DLS analysis and potential measurements did not reveal any significant changes in complex characteristics, size or surface charge, over a period of 4-day incubation at 37° C., in HEPES or transfection medium". Accordingly it is understood that the binary complexes are stable over several days.

The present inventors further investigated whether such binary complexes could be formed with divalent cations other than calcium, and be effective for delivery of siRNA. The results presented in Example 12 (FIG. 13) indicate that the replacement of $Ca^{2+}$ by $Mg^{2+}$ and $Ba^{2+}$ led to the assembly of nanocomplexes of similar physical features (size, surface charge) as $Ca^{2+}$-siRNA nanocomplexes, yet these other bivalent cation nanocomplexes were toxic to cells (FIG. 14) at non-physiological concentrations and were not taken up by the cells to the same extent as those prepared with $Ca^{2+}$ and no siRNA-induced target-gene silencing was demonstrated (FIG. 15). Thus, it appears that calcium ions are critical not only as bridges for neutralizing the siRNA molecules and assembly of the nanocomplex but also as an important determinant inducing the cell internalization of the nanocomplexes and siRNA release from the endosome. In view of the foregoing it was concluded that only calcium cations could be used for delivery of genes in order to control gene expression.

Thus, in yet a further aspect, the present invention provides an anionic complex which is a binary complex comprising a calcium ion, which is derived or dissociated from a strong electrolyte, and a nucleic acid and lacking an anionic (or cationic) polymer, wherein said binary complex is in the form of nanoparticles and capable of forming a colloidal suspension. The term "colloidal suspension refers to a suspension in which the nanoparticles do not precipitate or sink to the bottom of the vehicle holding the solution. The source of the calcium in the binary complex is not calcium phosphate and therefore the binary complex is essentially lacking phosphate ions.

As explained above, the anionic complex is stable.

In some embodiments, the zeta potential, or surface charge of the anionic complex of the invention is more negative than −5 mV.

The present invention further provides a method for producing the binary complex, the method comprising mixing said nucleic acid with a salt of a calcium ion that becomes a strong electrolyte in zwitterionic buffer at physiological pH. Thus, it is evident that the method for producing the binary complex could be considered a first step in the method for producing the polyplex described above.

The nucleic acid being part of the binary complex may be selected from the group consisting of DNA, such as a plasmid DNA (pDNA) or an oligodeoxynucleotide (ODN), or RNA such as siRNA, mRNA or miRNA. In some embodiments, the nucleic acid is siRNA.

According to Example 10, the diameter of the complex is about 80 nm. In some embodiments, the diameter of the complex is 50-200 nm. In some embodiments, the diameter of the complex is 50-100 nm, e.g. about 80 nm.

The final concentration of $Ca^{2+}$ may vary and be above 4 mM, depending, inter alia, on the cell type targeted for introduction of the polyplexes. In certain embodiments, the calcium concentration is about 5 mM.

In certain independent embodiments, the salt is $CaCl_2$, the zwitterionic buffer is HEPES, and the nucleic acid is siRNA. In certain embodiments, the calcium concentration is about 5 mM and the siRNA concentration is about 50 nM siRNA. In other embodiments, the molar ratio of $Ca^{2+}$: siRNA is $8 \times 10^4$:1 and above.

Thus, the binary complex of the present invention may be used in the delivery of a nucleic acid to cells. Additionally, the binary complex of the present invention may be used in order to silence or modulate the expression of genes in the cells to which the nucleic acids are delivered.

In some embodiments, the nucleic acid is capable of silencing of a gene associated with a disease, disorder or condition selected from the group consisting of cancer or metabolic, neurodegenerative, cardiovascular, infectious or inflammatory disease or disorder.

Each one of the pharmaceutical compositions and methods of administration as described above with regard to the polyplex, and any combination thereof, also apply to the binary complex.

According to a further aspect, the present application provides a method for the preparation of the anionic complex of the present invention, comprising mixing said nucleic acid with a salt of a divalent cation that is a strong electrolyte in zwitterionic buffer at physiological pH.

The terms "strong electrolyte" and "physiological pH" are as defined herein above.

The invention will now be illustrated by the following non-limitative examples.

EXAMPLES

Experimental
Materials:
(1) Anionic polymers—Alginate (sodium salts of VLVG (very low viscosity sodium alginate)) (30-50 kDa) or LVG (low viscosity sodium alginate, 80-120 kDa), both >65% guluronic acid content) was purchased from NovaMatrix, FMC BioPolymer, Drammen, Norway. Hyaluronan (sodium salt, 51 or 150 kDa) was from Lifecore Biomedical, Chaska, Minn. Alginate-sulfate (Alg-S) or hyaluronan-sulfate (HA-S) were prepared from alginate (VLVG or LVG) or hyaluronan as previously described (Freeman et al., 2008, *Biomaterials* 29, 3260-3268). Monoamino nanogold (1.4 nm) (Au—$NH_2$) particles were linked to hyaluronan-sulfate using carbodiimide chemistry as described (Polyak, et al., 2004, *Biomacromolecules* 5, 389-396), for TEM imaging. Fluorescent labeling of hyaluronan-sulfate with HiLyte Fluor 555 nm amine dye (Anaspec, Fremont, Calif., referred to herein as "555 nm-labeled") was performed using carbodiimide chemistry (Polyak, et al., 2004, *Biomacromolecules* 5, 389-396). Heparin (sodium salt, from porcine intestinal mucosa, 7.5 kDa) was purchased from Sigma Chemical Co. (St. Louis, Mo.).

(2) RNAse A (Life Technologies)

(3) Double stranded siRNA sequences: eGFP (SEQ ID NOs: 1+2), STAT3 (SEQ ID NOs: 3+4) and non-targeting (NT, SEQ ID NOs: 5+6), Cy3− or Cy5−(both SEQ ID NOs: 7+8) labeled siRNAs as well as gold-labeled siEGFP (SEQ ID NOs: 1+2) were purchased from IDT (Coralville, Iowa), GAPDH was purchased from the Dharmacon siGENOME SMARTpool collection (Lafayette, Colo.), pEGFP-N1 (GenBank Accession #U55762) was a kind gift from Prof Ziv Reich (Weizmann Institute of Science, Rehovot, Israel.

(4) Cell culture reagents (Dulbecco's modified Eagle's medium (DMEM), RPMI, L-glutamine, penicillin/streptomycin, heat inactivated FBS) were from Biological Industries (Kibbutz Beit-Haemek, Israel). Bafilomycin, Dynasore, PitStop2®, YM201636, and Genistein were purchased from Abcam. Fluorescent labeling of plasmid DNA was performed using Label IT Nucleic Acid Labeling kit (Mirus Bio, Madison, Wis.), according to manufacturer's instructions.

(5) Other materials: Monoamino Nanogold® labeling reagent ($NH_2$—Au, mean diameter 1.4 nm) was purchased from Nanoprobes (Yaphank, N.Y.). Other reagents, unless specified otherwise, were from Sigma. All reagents were of analytical grade. Human recombinant interleukin-6 (IL-6) was purchased from Peprotech (Rocky Hill, N.J.).

Animals

Balb/c mice were housed and bred at the animal facility of the Soroka University Medical Center, Beer Sheva and maintained in autoclaved cages with autoclaved bedding, food and water. All surgical and experimental procedures were reviewed and approved by the Institutional Animal Care and Use Committee (IACUC) of Ben-Gurion University of the Negev. For isolation of peritoneal macrophages, male mice aged 8-10 weeks were used.

Cell Lines

CT26 eGFP expressing cells—CT26 mouse colon carcinoma cells, stably transfected with enhanced green fluorescence protein (eGFP) were cultured in DMEM supplemented with 10% FBS, 2 mM L-glutamine, 500 µg/ml G418, and 1% penicillin/streptomycin. The cells were incubated at 37° C. in a humidified air atmosphere containing 5% $CO_2$.

Mouse embryonic fibroblasts (MEF)—Mouse embryonic fibroblasts were cultured in DMEM supplemented with 10% FBS, 2 mM L-glutamine, and 1% penicillin/streptomycin. The cells were incubated at 37° C. in a humidified air atmosphere containing 5% $CO_2$.

HepG2 cells—HepG2 cells (human hepatocellular carcinoma cell line) were cultured in DMEM supplemented with 10% FBS, 2 mM L-glutamine, and 1% penicillin/streptomycin. The cells were incubated at 37° C. in a humidified air atmosphere containing 5% $CO_2$.

U266 cells—U266 cells (human multiple myeloma cell line) were cultured in RPMI 1640 medium supplemented with 20% FBS, 2 mM L-glutamine, and 1% penicillin/streptomycin. The cells were incubated at 37° C. in a humidified air atmosphere containing 5% $CO_2$.

Peritoneal Macrophages Cultivation

Thioglycollate (Hylabs, Rehovot, Israel) (2.5 mL) was injected into the peritoneum of 8-10-week old Balb/c mice. Four days later, the mice were sacrificed using isofluoran, and the peritoneum was washed three times with cold PBS to collect cell lavage. Peritoneum lavage was centrifuged at 150 g at 4° C. for 6 min. Cells were resuspended in culture medium (RPMI 1640 supplemented with 10% FBS, 1% L-Glu, 1% Pen-Strep) and seeded at a density of $0.5 \times 10^6$ cells per well in 12-well tissue culture plates for subsequent silencing experiments, and in chamber slides at a density of 150,000 (cells/well) for subsequent confocal microscopy. Cells were allowed to adhere for 2 h after seeding, after which time the wells were washed with HBSS and culture medium was added.

Preparation of Anionic Polymer-based Nucleic Acid Polyplexes

Anionic Polyplexes of siRNA

Solutions of HEPES (10 mM), $CaCl_2$ (1M), and siRNA (10 µM), were freshly prepared in DEPC-treated water. Stock anionic polymer solutions were prepared:

Alginate (Alg) and alginate-sulfate (Alg-S): 50 µg/ml and 300 µg/ml, in 10 mM HEPES solution Hyaluronan (HA) and hyaluronan-sulfate (HA-S): 50 µg/ml and 500 µg/ml, in 10 mM HEPES solution Preparation of the anionic polyplexes: Equal volumes of siRNA (10 µM) and $CaCl_2$ (1M) were mixed together by vortexing (moderate speed) for 30 sec and were incubated for 20 min at room temperature (RT). Then, equal volumes of the anionic polymers were added and mixed by vortexing (moderate speed) for 30 sec, followed by 30 min incubation at RT prior to use. The anionic siRNA polyplexes were freshly prepared before analysis or use. Same procedure of polyplex preparation was followed in all experiments. For studies in macrophages and U266 cells, initial $CaCl_2$ solution of 200 mM was used.

Anionic Polyplexes of miRNA

Solutions of HEPES (10 mM), $CaCl_2$ (1M), and miRNA (10 µM), were freshly prepared in DEPC-treated water. Stock anionic polymer solutions were prepared:

Alginate (Alg) and alginate-sulfate (Alg-S): 50 µg/ml and 300 µg/ml, in 10 mM HEPES solution Hyaluronan (HA) and hyaluronan-sulfate (HA-S): 50 µg/ml and 500 µg/ml, in 10 mM HEPES solution Preparation of the anionic miRNA polyplexes: Equal volumes of miRNA (10 µM) and $CaCl_2$ (1M) were mixed together by vortexing (moderate speed) for 30 sec and were incubated for 20 min at room temperature (RT). Then, equal volumes of the anionic polymers were added and mixed by vortexing (moderate speed) for 30 sec, followed by 30 min incubation at RT prior to use. The anionic miRNA polyplexes were freshly prepared before analysis or use.

Anionic Polyplexes of DNA

Solutions of HEPES (10 mM), $CaCl_2$ (400 mM), and DNA (100 µg/ml), were freshly prepared in DEPC-treated water. Stock anionic polymer solutions were prepared:

Alginate (Alg) and alginate-sulfate (Alg-S): 50 µg/ml and 500 µg/ml, in 10 mM HEPES solution Hyaluronan (HA) and hyaluronan-sulfate (HA-S): 50 µg/ml and 500 µg/ml, in 10 mM HEPES solution Preparation of the anionic polyplexes: Equal volumes of DNA (100 µg/ml) and $CaCl_2$ (400 mM) were mixed together by vortexing (moderate speed) for 30 sec and were incubated for 20 min at room temperature (RT). Then, equal volumes of the anionic polymers were added and mixed by vortexing (moderate speed) for 30 sec, followed by 30 min incubation at RT prior to use. The anionic DNA polyplexes were freshly prepared before analysis or use.

Preparation of Nucleic Acid Binary Complexes

Anionic Binary Complexes of siRNA

Solutions of HEPES (10 mM, pH 7.4), $CaCl_2/MgCl_2/MnCl_2/BaCl_2/ZnCl_2$/(1M stock concentration), and siRNA (10 µM stock concentrations), were freshly prepared in DEPC-treated water. Equal volumes of siRNA and $CaCl_2$ were mixed together by vortexing for 30 sec and incubating for 20 min at room temperature (RT). Then, an equal volume of 10 mM HEPES was added and mixed by vortexing for 30 s, followed by 30 min incubation at RT prior to use. The complexes were freshly prepared before analysis or use and diluted to the final concentration indicated, unless stated otherwise.

Transmission Electron Microscopy

Complexes composed of $Ca^{2+}/Mg^{2+}/Mn^{2+}$/or $Ba^{2+}$-siRNA nanocomplexes (using gold-labeled siRNA) were diluted 1:10 in HEPES solution (10 mM). The final concentration of each component in the complexes was as follows: 250 nM siRNA, 2.5 µM HA-S. Five µL of each sample was placed on carbon-coated films on copper EM grids hydrophilized by glow discharge. The excess liquid was blotted and the grids were allowed to dry at RT for 4 h. The samples were imaged at RT using a FEI Tecnai 12 $G^2$ TWIN TEM (Gatan model 794 CCD, bottom mounted) at acceleration voltage of 120 kV. Specimens were studies in a low-dose imaging mode to minimize beam exposure and electron beam radiation damage. Images were recorded digitally using the Digital Micrograph 3.6 software (Gatan, Munich, Germany). Particle size measurements were performed using ImageJ 1.49b software (U. S. National Institutes of Health, Bethesda, Md., http://imagej.nih.gov/ij/).

Cryogenic Transmission Electron Microscopy (Cryo-TEM)

Complexes composed of gold-labeled HA-S were prepared as described above (2.5 µM siRNA, 25 µM HA-S). Thin (~0.25 µm) specimens of the liquid complex solution were deposited, under controlled humidity and temperature, on perforated carbon films supported on copper grids, which were hydrophilized by glow discharge. The excess liquid was blotted with filter paper, and the specimen was vitrified by rapid plunging into liquid ethane precooled to its freezing point with liquid nitrogen in a controlled-environment vitrification system (Bellare et al., 1988). Such rapid cooling causes water to vitrify, and thus prevents microstructural changes by ice crystallization (Borgstrom et al., 1996). The samples were examined at $-178°$ C. using a FEI Tecnai 12 $G^2$ TWIN TEM (Gatan model 794 CCD, bottom mounted) equipped with a Gatan 626 cryo-holder. Specimens were studied in a low-dose imaging mode to minimize beam exposure and electron beam radiation damage. Images were recorded digitally using the Digital Micrograph 3.6 software (Gatan).

Ethidium Bromide Exclusion Assay of siRNA or DNA-containing Anionic Polyplexes for Serum Stability and Heparin Displacement The effect of serum or polyanionic polymer (heparin) on the stability of (HA-S)-Ca-siRNA polyplex was evaluated by ethidium bromide (EtBr) exclusion assay. Polyplexes were incubated with 200 µl serum (10%, v/v) or heparin (at 2:1 and 5:1 w/w ratio to siRNA) for 1 h, at RT. Next, 15 µl of each sample were mixed with EtBr solution at a concentration matched to maintain 1:1 molar ratio between phosphate groups and EtBr monomer. Samples were incubated in RT for 30 min and then read at Ex (excitation) 535 nm/Em (emission) 595 nm using Synergy Mx microplate reader (Biotek, Winooski, Vt.). Relative fluorescence units (RFU) were normalized to free siRNA sample, taken as 100%.

Ethidium Bromide and Ribogreen Exclusion Assays to Evaluate Complexation

The complexation of siRNA with the various cations in the binary complexes was evaluated by ethidium bromide (EtBr) and by Ribogreen exclusion assays. For evaluating complexation, various formulations were mixed with EtBr solution at a concentration matched to maintain a 1:1 molar ratio between the phosphate groups and EtBr monomer. Samples were incubated at RT for 30 min and then read at Ex (excitation) 535 nm/Em (emission) 595 nm, using a SynergyMx microplate reader (Biotek, Winooski, Vt.). Relative fluorescence units (RFU) were normalized to free siRNA sample, taken as 100%. For the Ribogreen assay, 10 µl of stock solution were diluted in 90 µl of 10 mM HEPES and added to 100 µl of Ribogreen diluted in 10 mM HEPES, in a 1:200 v/v ratio. Samples were incubated for 5 min at RT and then read at Ex (excitation) 480 nm/Em (emission) 520 nm, using a SynergyMx microplate reader (Biotek, Winooski, Vt.). Relative fluorescence units (RFU) were normalized to free siRNA sample, taken as 100%.

Nuclease Protection Assay of siRNA

The stability of naked siRNA or siRNA in HA-S polyplex against RNase A digestion, with or w/o serum presence, was investigated. Aliquots of 20 µl, with or w/o serum (10% final, v/v), containing 0.6 µg siRNA, were incubated with 20 µl of enzyme, containing 0.032 µg RNase A, for 24 h at 37° C. Afterwards, EtBr exclusion assay was used to quantify the results, as detailed above.

Assessment of siRNA Uptake by Confocal Microscopy

For visualizing cellular uptake of siRNA anionic complexes and internalization of siRNA (Cy5 or Cy3-labeled) and HA-S (555 nm-labeled), confocal microscopy was used. Cells were seeded in chamber slides (ibidi, Planegg, Germany) at a cell density of 50,000 cells per well in culture medium supplemented with 10% FBS, L-glutamine and antibiotics. Twenty-four hours post seeding, the cells were washed once with PBS and treated with fluorescently labeled siRNA-anionic complexes that were freshly diluted (1:50) in transfection medium (culture medium w/o FBS). Two hours post transfection the medium was removed and the cells were washed once with PBS (with $Ca^{2+}$ and $Mg^{2+}$). At indicated time points, to remove extracellular polyplexes, cells were then incubated with CellScrub buffer (Genlantis, San-Diego, Calif.) for 15 min at RT, and were then washed with PBS (w/o $Ca^{2+}$ and $Mg^{2+}$). Nuclei were stained with NucBlue® (for live, unfixed cells) (Life Technologies). Images were taken using a Nikon Cisi laser scanning confocal microscope (LSCM).

Assessment of siRNA Uptake by Imaging Flow Cytometry

Cells were seeded in 12-well culture plate at a cell density of 500,000 cells per well, supplemented with 10% FBS, L-glutamine and antibiotics. Twenty-four hours post seeding, the cells were washed once with PBS and treated with fluorescently labeled siRNA-anionic complexes (Cy5-labeled siRNA, 555 nm-labeled HA-S), that were freshly diluted (1:50) in transfection medium (culture medium w/o FBS). For the compensation and analysis, single labeled and double-labeled polyplexes were used: Two hours post transfection, the medium was removed and the cells were washed once with PBS (with $Ca^{2+}$ and $Mg^{2+}$). To remove extracellular polyplexes, cells were then incubated with CellScrub buffer for 15 min at RT, and were later washed with PBS (w/o $Ca^{2+}$ and $Mg^{2+}$). Cells were trypsinized, resuspended in culture medium and centrifuged (1000 rpm for 5 min). Cells were washed twice by resuspension in FACS buffer (PBS containing 2% FBS) and recovered by centrifugation (650 g for 5 min). The collected cells was then resuspended in FACS buffer and were analyzed using ImageStreamX Mark II (Amnis, Seattle, Wash.). Cell acquisition and analysis were performed using IDEAS Application, version 6.0.

Assessment of GFP Expression by Imaging Flow Cytometry

Cells were seeded in a 12-well culture plate at a cell density of 100,000 cells per well, supplemented with 10% FBS, L-glutamine and antibiotics. Twenty-four hours post seeding, the cells were washed once with PBS and treated with pEGFP-anionic polyplexes that were freshly diluted (1:50) in transfection medium (culture medium w/o FBS). Four hours post transfection, the medium was removed and the cells were washed once with PBS (with $Ca^{2+}$ and $Mg^{2+}$), and incubated for 48 hours to allow GFP expression. Cells were trypsinized, resuspended in culture medium and centrifuged (1000 rpm for 5 min). Cells were washed twice by resuspension in FACS buffer (PBS containing 2% FBS) and recovered by centrifugation (650 g for 5 min). The collected cells was then resuspended in FACS buffer and were analyzed using ImageStreamX Mark II (Amnis, Seattle, Wash.). Cell acquisition and analysis were performed using IDEAS Application, version 6.0.

Cell Viability

Anionic polyplex effect on cell viability was assessed using PrestoBlue cell viability assay (Life Technologies, Carlsbad, Calif.). This assay is based on the live cell's ability to reduce resazurin (non-fluorescent) to resorufin (fluorescent). PrestoBlue working solution was prepared by dilution of PrestoBlue reagent 1:10 in cell culture medium. At selected time points after transfection, the medium was aspirated and cells were washed once with PBS and were then incubated with PrestoBlue working solution for 1 h at 37° C. and 5% $CO_2$. Fluorescent intensity was measured using Synergy Mx microplate reader (Biotek, Winooski, Vt.) at an excitation wavelength of 560 nm and emission wavelength of 590 nm. The percentage of cell viability was obtained after normalizing the data to untreated cells. In addition, we assessed mRNA levels of stress-inducible genes (Hmox-1, HSP70, and Gclc) by quantitative real-time PCR (qPCR) (see below).

In Vitro Silencing Studies

CT26 eGFP-expressing cells were seeded in 24-well cell culture plate at a cell density of 50,000 cells per well in DMEM culture medium supplemented with 10% FBS, L-glutamine and antibiotics. Twenty-four hours post seeding, the cells were washed once with PBS and incubated with eGFP siRNA-containing anionic polyplexes that were freshly diluted (1:50) in transfection medium (culture medium w/o FBS). Final siRNA concentration was 50 nM. Three hours post incubation the medium was removed, and the cells were washed and supplemented with complete medium. Twenty-four hours post transfection, mRNA level of eGFP was analyzed using quantitative real-time PCR. Additionally, expression level of eGFP was analyzed by flow cytometry at several time points (24, 48, 72 h post transfection) (see below).

Similarly, the silencing efficacy in other cell models was examined. In MEFs and primary mouse macrophages siRNA against GAPDH was used. In addition, silencing studies of STAT3 were performed in two human cell models, HepG2 (hepatocellular carcinoma) and U266 (multiple myeloma) cells. Silencing efficiency was evaluated twenty-four hours post transfection, by using quantitative real-time PCR.

Quantification of mRNA Levels by qPCR

The mRNA levels of eGFP, GAPDH, and STAT3 were quantified by real-time PCR. Twenty-four hours post transfection, Total RNA was isolated using the EZ-RNA RNA purification kit (Biological Industries, Beit Haemek, Israel), and 500 ng of RNA from each sample was reverse transcribed into cDNA using the High Capacity cDNA Reverse Transcription Kit (Applied Biosystems, Foster City, Calif.). For gene expression analysis, mRNA levels were determined by real-time PCR using StepOnePlus™ Applied detection system (Applied Biosystems) according to the instructions of the manufacturer. Analysis of eGFP mRNA expression levels was performed using the SYBR green Master mix (Applied Biosystems) and data was analyzed by delta Ct method using PPIA as house-keeping gene.

TABLE 1 primer sequences for gene expression analysis using SYBR ® Green PCR maste rmix

| Gene symbol | Primers | | SEQ ID NOs |
|---|---|---|---|
| eGFP | Forward: | AGGAGCGCACCATCTTCTTC | 9 |
| | Reverse: | ATGATATAGACGTTGTGGCTGTTG | 10 |
| PPIA | Forward: | CGACTGTGGACAGCTCTAAT | 11 |
| | Reverse: | CCTGAGCTACAGAAGGAATG | 12 |
| SAA1 | Forward: | CTGCAGAAGTGATCAGCG | 13 |
| | Reverse: | ATTGTGTACCCTCTCCCC | 14 |
| Fibrinogen | Forward: | TAGCCAGCTTACCAGGATGG | 15 |
| | Reverse: | GGCTGTTCCTCTGTATTTGTTCA | 16 |
| ACTB | Forward: | ATAGCACAGCCTGGATAGCAACGTAC | 17 |
| | Reverse: | CACCTTCTACAATGAGCTGCGTGTG | 18 |

PPIA - peptidylprolyl isomerase A; SAA1 (serum amyloid A1)

Gene expression analysis of GAPDH and STAT3 was performed using TaqMan gene expression assays using HPRT and ACTB as house-keeping genes.

TABLE 2

TaqMan gene expression assays for gene expression analysis

| Gene symbol | Gene name | Assay ID |
|---|---|---|
| Gapdh | glyceraldehyde-3-phosphate dehydrogenase | Mm99999915_g1 |
| Hprt | hypoxanthine guanine phosphoribosyl transferase | Mm00446968_m1 |
| Hmox-1 | heme oxygenase (decycling) 1 | Mm00516005_m1 |
| Hspa1b/Hsp70 | heat shock protein 70 | Mm03038954_s1 |
| Gclc | glutamate-cysteine ligase; catalytic subunit | Mm00802655_m1 |
| Ppia | peptidylprolyl isomerase A | Mm02342430_g1 |
| Stat3 | signal transducer and activator of transcription 3 | Hs00374280_m1 |
| ACTB | actin, beta | Hs99999903_m1 |

Flow Cytometry Analysis of eGFP Expression for Silencing Evaluation

The silencing efficacy of eGFP entrapped in anionic polyplexes was assessed by flow cytometry (FACS) analysis at different time points (24, 48, 72 h) post transfection. Cells were trypsinized, resuspended in culture medium and centrifuged (650 g for 5 min). Cells were washed twice by resuspension in FACS buffer (PBS containing 2% FBS) and recovered by centrifugation (650 g for 5 min). The collected cells was then resuspended in FACS buffer and transferred to a flow cytometer tube (BD Biosciences, San Jose, Calif.). Cell acquisition and analysis (10,000 events) were performed using a FACS Calibur (BD Biosciences) machine, utilizing Cellquest Pro software (BD Biosciences).

Results were calculated using the geometric mean fluorescence (GEO mean), and silencing efficiency percentage was obtained using the formula:

$$\% \, EGFP = \frac{EGFP \text{ fluorescence of transfected cells}}{EGFP \text{ fluorescence of control cells}} \times 100$$

Silencing efficiency = $100 - (\% \, eGFP)$

Statistical Analysis

Statistical analysis was performed with GraphPad Prism version 5.03 for Windows (GraphPad Software, San Diego, Calif.). All variables are expressed as mean±SEM. EtBr exclusion assay results, viability, qPCR of stress-related genes, qPCR of eGFP, STAT3 and GAPDH silencing were compared by one-way ANOVA with Dunnett's post-hoc test for multiple comparisons to control group. RNase and blood plasma stability data, eGFP FACS results and densitometric analysis of total STAT3 immunoblotting were compared by a general linear 2-way ANOVA. Dunnett's correction was used to assess the significance of predefined comparisons to control group. Phosphorylated STAT3 levels, and APR (SAA1 and fibrinogen) gene expression were compared by unpaired t test. P<0.05 was considered statistically significant.

Serum Stability

Complex stability in rat blood plasma was also evaluated using EtBr exclusion assay. Samples of (HA-S)-Ca-siRNA complexes (2.5 μM siRNA, 5 mM $Ca^{2+}$, 2.5 μM HA-S) and naked siRNA were mixed with fresh rat blood plasma to give 50% (v/v), and incubated at 37° C. After 24 h samples were removed, incubated with EtBr solution and analyzed as detailed above.

Regulation of Acute Phase Response (APR) by STAT3 Silencing in Human HepG2 Hepatocytes by (HA-S)-Ca-siRNA Complexes.

HepG2 cells were selected as a cellular model for studying the regulation of acute phase response by STAT3 silencing using (HA-S)-Ca-siRNA complexes.

Primarily, cellular internalization of (HA-S)-Ca-siRNA complexes in HepG2 cells was evaluated using an imaging flow cytometer, as described above. Briefly, HepG2 cells were treated with labeled (HA-S)-Ca-siRNA anionic complexes [Cy-5-labeled siRNA (50 nM), HiLyte Fluor 555 nm—labeled HA-S (500 nM)]. Two hours post transfection, cellular uptake images of (HA-S)-Ca-siRNA complexes in HepG2 cells were captured by Amnis ImageStreamX flow cytometer and level of internalization of siRNA-Cy5 was assessed using IDEAS Application, version 6.0.

To examine the capability of (HA-S)-Ca-siRNA complexes to induce STAT3 gene knockdown, we treated HepG2 cells with (HA-S)-Ca-siSTAT3 complexes (50 nM siSTAT3, 50 nM HA-S). Twenty-four hours post transfection, mRNA level of STAT3 was analyzed using qPCR (as described above).

Functional silencing study was carried out in HepG2 cells under IL-6 stimulation. Cells were treated with (HA-S)-Ca-siSTAT3 complexes (50 nM siSTAT3, 50 nM HA-S) for 3 h, and then incubated for 48 h in culture medium. Cells were serum starved (0.1% FBS) for 8 h prior to IL-6 addition (20 ng/mL) for 30 min. STAT3 protein level and activation (phosphorylation on Tyr705) extent was analyzed by Western immunoblotting, as detailed below.

Finally, gene expression analysis of IL-6-induced acute phase response genes: SAA1 (serum amyloid A1) and fibrinogen was performed using qPCR. HepG2 cells were treated with (HA-S)-Ca-siSTAT3 complexes (50 nM siSTAT3, 50 nM HA-S) for 3 h, and then incubated for 24 h in culture medium prior to IL-6 (20 ng/mL) addition. Twenty-four hours later, mRNA levels of SAA1 and fibrinogen were analyzed using qPCR (as described above).

Western Blot Analysis of STAT3 Activation

The extent of STAT3 activation following STAT3 silencing and IL-6-induced stimulation was evaluated by Western blotting. At the end of the experiment, the medium was discarded and the cell-seeded wells were snap-frozen in liquid nitrogen and transferred to a −80° C. The cells were lysed with ice-cold radioimmunoprecipitation (RIPA) buffer (Cell Signaling, Danvers, Mass.) supplement with 1 mM PMSF. Total protein quantification was performed using micro BCA protein assay (Pierce Biotechnology, Rockford, Ill.). Proteins (30 μg/lane) were separated in mini-PROTEAN TGX gel (Bio-Rad, Hercules, Calif.), and then transferred to nitrocellulose membranes (Bio-Rad). After blocking, the membranes were incubated with anti-phospho-Tyr705-STAT3 and anti-total STAT3 antibodies (Cell Signaling, Danvers, Mass.). Proteins were visualized using anti-rabbit HRP-conjugated secondary antibodies (Pierce Biotechnology), and standard enhanced chemiluminescence (ECL) procedure (Biological Industries, Kibbutz Beth HaEmek, Israel). The signal was detected using ImageQuant LAS4000 image analyzer (GE Healthcare, Pittsburgh, Pa.). Densitometric analysis was carried out using ImageJ 1.49b software (U.S. National Institutes of Health, Bethesda, Md., http://imagej.nih.gov/ij/). Band intensity was normalized to GAPDH.

Cell Uptake of Plasmid DNA (pDNA) Complexes

CT26 cells ($1\times10^5$ per well) were seeded into 12-well plates and grown overnight. The cells were then incubated at 37° C. with Cy3-labeled (HA-S)-Ca-pDNA (pEGFP-N1) complexes diluted (1:50) in RPMI 1640 with 1% L-glu (v/v) and 1% PS (v/v) for 3 hours. The cells were then trypsinized, washed with cold PBS, and resuspended in PBS with 2% FBS (v/v). Imaging flow cytometry analysis was done using Amnis ImageStreamX Mark II (Seattle, Wash.). Cell acquisition and analysis were performed using IDEAS Application, version 6.0.

Optimization of Inhibitor Concentration for Endocytosis Inhibition

We conducted preliminary studies to choose the inhibitor concentration tolerated by the cells. EGFP-transfected CT26 cells were seeded on 12-well plates, at a density of 150,000 cells per well in culture medium. Twenty-four h post-seeding, the cells were washed once with PBS and then were incubated with inhibitors (Table 3) in transfection medium for 3 h. In positive controls, cells were treated with $H_2O_2$. The cells were trypsinized, washed twice by resuspension in FACS buffer (PBS containing 2% FBS, v/v) and recovered by centrifugation (650×g for 5 min, at 4° C.). Cell viability was assayed by adding 7-AAD (7-aminoactinomycin D) solution to cells suspended in FACS buffer to reach a final concentration of 20 ug/ml and the cells were incubated for 30 min on ice in the dark. The collected cells were then resuspended in FACS buffer and were analyzed using ImageStreamX Mark II (Amnis, Seattle, Wash.). Cell acquisition and viability analysis were performed using IDEAS Application, version 6.0.

TABLE 3

Inhibitors, their functions and concentration

| Inhibitor Name | Inhibits pathway | Concentration range | Chosen concentration |
|---|---|---|---|
| Dynasore | Dynamin dependent | 10-100 μM | 50 μM |
| PitStop2 ® | Clathrin dependent | 5-30 μM | 15 μM |
| Genistein | Caveolae dependent | 30-150 μM | 60 μM |
| Nifedipine | L-type Calcium channel blocker | 10-50 μM | 20 μM |
| $CdCl_2$ | Competitive calcium antagonist | 10-100 nM | 50 nM |
| Bafilomycin A1 | V-ATPase inhibitor | 50-200 nM | 75 nM |
| YM201636 | Maturation of early endosome | 1-5 μM | 2 μM |

Inhibition Studies

EGFP-transfected CT26 cells were seeded on chamber slides and on 24 well plates. The cells were pre-incubated for 30 min, at 37° C., with each of the following inhibitors in the chosen concentration (Table 3). Then the cell monolayers were rinsed twice and subsequently were co-incubated with the $Ca^{2+}$-siRNA nanocomplexes [siRNA (50 nM)] and the inhibitors, for 3 h, at 37° C. This was done to ensure the effect of the inhibitors for the entire transfection period as the inhibitors are reversible. We examined the effect of inhibitors on cell uptake of the nanocomplexes, diluted 1:50, using Cy3-siRNA and visualization by confocal microscopy, as described above and their effect on gene silencing by nanocomplexes of $Ca^{2+}$-si-eGFP followed by FACS analysis, as described above.

Dynamic Light Scattering (DLS), and Zeta (ζ) Potential Measurements

Particle size distribution and mean diameter of the nucleic acid-containing anionic complexes were measured on a CGS-3 (ALV, Langen, Germany) instrument. Samples were diluted 1:50 in HEPES solution (10 mM) and were analyzed by scattered laser light (He—Ne laser, 20 mW, 632.8 nm) and detected under an angle of 90°, during 10 s for 20 times, at 25° C. Correlograms were calculated by ALV/LSE 5003 correlator and fitted with version of the program CONTIN.

The surface charge (ζ potential, mV) of the anionic complexes was measured on a Zetasizer Nano ZS (Malvern Instruments Ltd., UK). Surface charge measured three times, each run at 25° C., 10 to 100 measurements were taken, depending on standard deviation. The zeta cell used was DTS 1060 (produced by Malvern Instruments Ltd., UK).

Example 1

Characterization of Nucleic Acid Anionic Polyplexes by Dynamic Light Scattering (DLS), and Zeta (ζ) Potential Measurements Particle diameter and zeta potential of the ternary anionic polyplexes were measured by DLS and zeta (ζ) potential was measured as described above. The results are presented in Table 4. HA: hyaluronic acid; Alg: alginate; HA-S: hyaluronan sulfate; Alg-S: alginate sulfate.

TABLE 4

Correlation of diameter and zeta potential with molecular weight of anionic polymer and ratio to siRNA

| Sample (molar ratio of anionic polymer to siRNA or plasmid DNA (pDNA)) | Average diameter (nm) | Average zeta potential (mV) |
|---|---|---|
| HA (51 kDa)-siRNA polyplex (4:1) | 102 | −5.6 |
| HA (150 kDa)-siRNA polyplex (0.7:1) | 81 | −8.4 |
| (HA-S)-Ca-siRNA polyplex (10:1) | 114 ± 32 | −7.98 ± 2.03 |
| (HA-S)-Ca-siRNA polyplex (1:1) | 128.5 ± 35 | −6.75 ± 1.48 |
| Alg (30 kDa)-siRNA polyplex (2.5:1) | 101 | −6.7 |
| Alg (100 kDa)-siRNA polyplex (0.7:1) | 123 | −7.9 |
| Alg-S-siRNA polyplex (6:1) | 105.1 ± 3.16 | −13.93 ± 5.25 |
| Alg-S-siRNA polyplex (10:1) | 137 | −8.4 |
| HA-S/pDNA polyplex (3000:1) | 146 | −11 |
| Alg-S-pDNA polyplex (3000:1) | 178 | −13 |

Example 2

Physical Characterization of Hyaluronan Sulfate (HA-S)-Ca-siRNA Complexes

The formation of nano-sized complexes was confirmed by dry and cryogenic transmission electron microscopy (TEM), using gold-labeled siEGFP or HA-S (FIG. 1). Dry-TEM analysis showed compact and nearly spherical complexes with similar appearance in micrographs obtained with gold-labeled siRNA (FIG. 1A) and gold-labeled HA-S (FIG. 1B), suggesting the presence of both components in the single complex. The observed sizes of the resulting complexes were lower compared to DLS measurements (~50 nm in diameter), due to the dehydration of the samples during preparation for dry analysis.

Figure 1C:
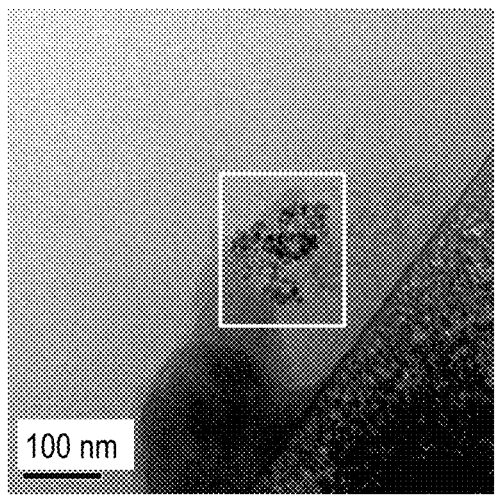
Figure 1D:
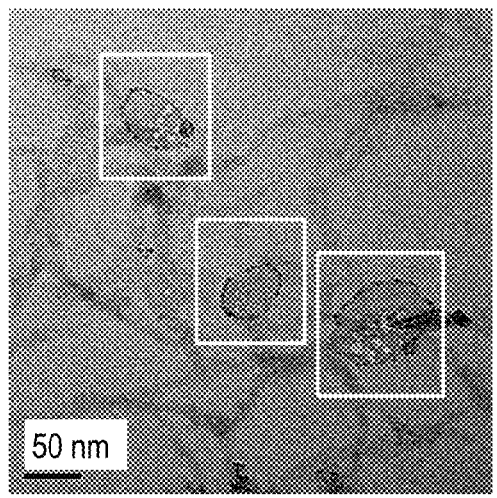

The important role of water molecules in complex formation and stabilization was evident in results obtained with cryo-TEM, which showed more comparable diameter size (~100 nm) to DLS (FIGS. 1C-1D). Importantly, cryo-TEM micrographs obtained with gold-labeled siRNA (FIG. 1C) and gold-labeled HA-S (FIG. 1D), revealed the specific spatial arrangement of complex components, with a "core" containing the siRNA, and a "shell" formed by HA-S polymer.

Example 3

Serum Stability and Heparin Displacement Assays

EtBr exclusion assay was used to quantify the degree of complexation of nucleic acids as an important parameter of polyplex stability. Effective complexation and physical masking of siRNA or pDNA should lead to exclusion of intercalating EtBr from siRNA, and, in turn, result in reduction of EtBr fluorescence. The effect of incubation of the anionic polyplexes with serum or with heparin on their stability was evaluated.

Figure 2A:
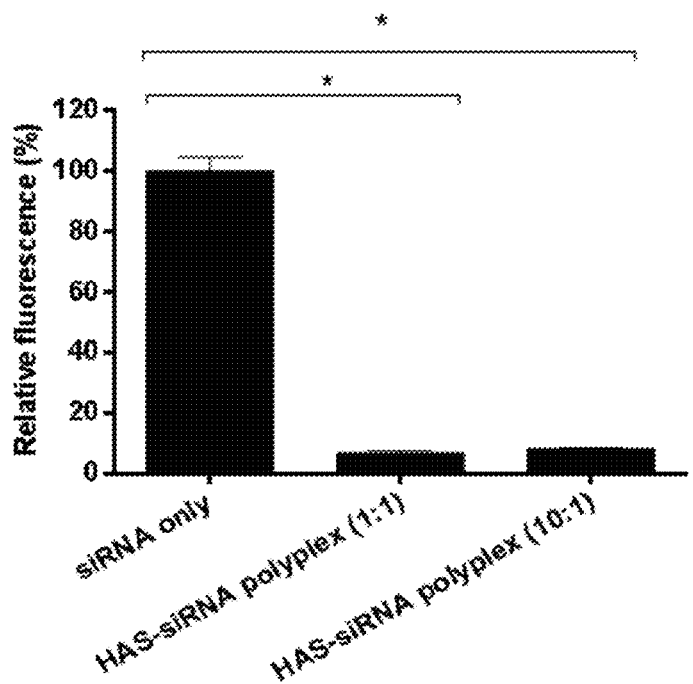
FIGS. 2A-2C show the effect of serum or heparin on polyplex stability. A. EtBr exclusion assay showing effective siRNA inclusion in HA-S polyplexes. Left to right: siRNA only, HA-S-Ca-siRNA polyplexes (1:1), (HA-S)-Ca-siRNA polyplexes (10:1). B. EtBr exclusion assay showing effective pDNA inclusion in HA-S or alginate sulfate (Alg-S) polyplexes (3000:1, molar ratio). Left to right: pDNA only, (HA-S)-Ca-pDNA polyplex, Alg-S-Ca-pDNA polyplex. C. Serum or heparin effect on polyplex dissociation and siRNA release. Left group (black): HA-S-Ca-siRNA polyplex molar ratio of HA-S to siRNA is 1:1; right group (gray): (HA-S)-Ca-siRNA polyplex molar ratio of HA-S to siRNA is 10:1; *-p<0.05. Left to right each group: no treatment, fetal bovine serum (FBS) 10%, heparin 2:1, heparin 5:1.
Figure 2B:
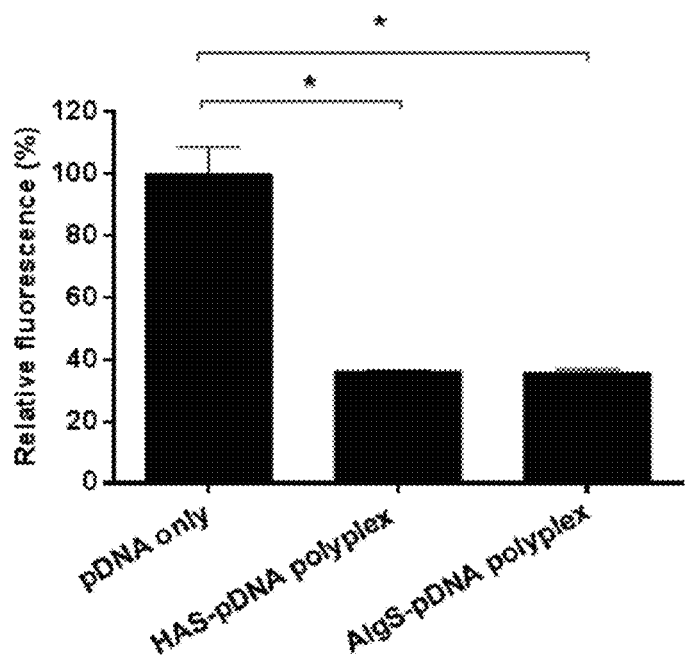

FIGS. 2A and 2B demonstrate effective siRNA or pDNA complexation while masking the nucleic acid therapeutics from the surroundings.

Figure 2C:
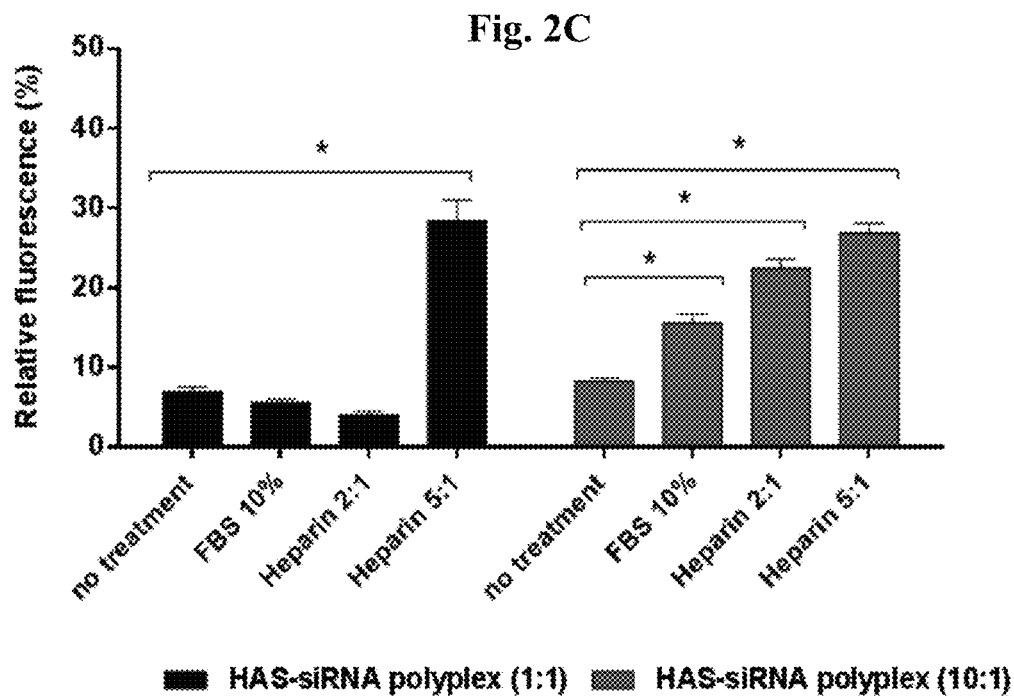

In anionic polyplexes composed of 1:1 molar ratio of HA-S and siRNA (using 5 mM $Ca^{2+}$), the presence of 10% (v/v) serum or low heparin (2:1) concentration in the medium had no effect on polyplex stability (FIG. 2C, left—black group of bars). Only in the presence of higher heparin concentration (5:1) there was partial decomplexation of the anionic polyplex and siRNA release (~30%). In polyplexes made from a greater molar ratio of HA-S to siRNA (10:1) the presence of serum or heparin resulted in minor (10-20%) siRNA release (FIG. 2C, right-gray group of bars). Collectively, these results indicate that the anionic polyplexes maintain their stability in serum and with competition of other anionic polymer (heparin).

Example 4

Stability of (HA-S)-Ca-siRNA Complexes

Figure 3A:
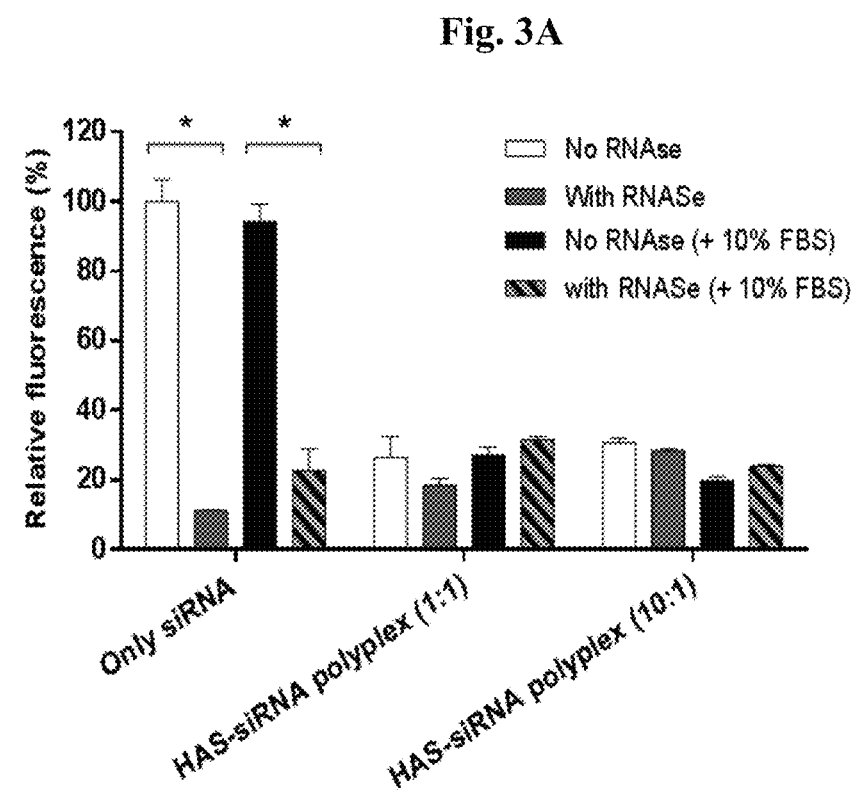
FIGS. 3A-3B Stability of (HA-S)-Ca-siRNA polyplexes after various treatments, evaluated by EtBr exclusion assay. A. Stability of (HA-S)-Ca-siRNA polyplexes against RNase A digestion. Samples of free siRNA (left group) or siRNA polyplexes (middle group: (HA-S)-Ca-siRNA molar ratio 1:1; right group: (HA-S)-Ca-siRNA molar ratio 10:1) were incubated for 24 h at 37° C., with or w/o serum (10%, v/v). *-p<0.05. Left to right each group: white bars: no RNAse; gray bars: with RNAse; black bars: no RNAse+10% FBS; hatched bars: with RNAse+10% FBS. *-p<0.05. B. Stability of siRNA in (HA-S)-Ca-siRNA complexes in rat blood plasma, after incubation at 37° C. for 24 h. P (interaction, 2-way ANOVA)=0.004. *-p<0.05 (Sidak's multiple comparisons test). Results are presented as relative fluorescence % to naked siRNA in the presence of EtBr, taken as 100%. Left to right: free siRNA (two black bars) without plasma or with plasma, (HA-S)-Ca-siRNA complex (two white bars) without plasma or with plasma.
Figure 3B:
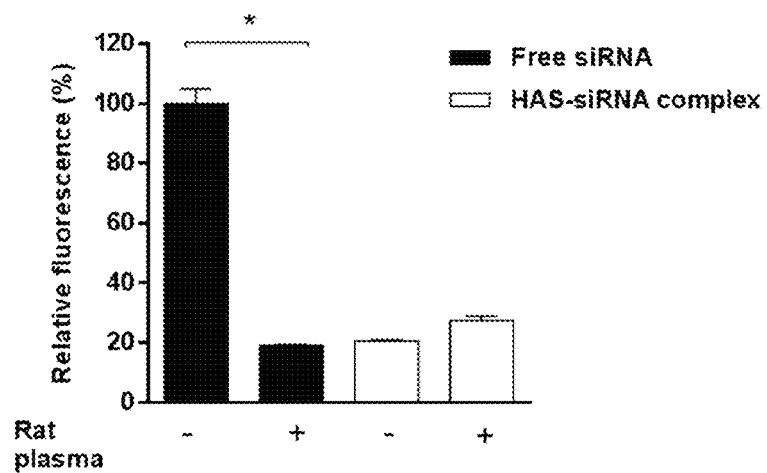

To further substantiate that siRNA is protected in the anionic polyplexes, the effect of RNase A, with or w/o serum, was analyzed by EtBr exclusion assay. Twenty-four hours after incubation in the presence of the enzyme, naked siRNA was completely degraded, while when in complex, it was fully protected from the RNAse activity (FIG. 3A). Finally, the stability of the complexes was also tested in blood plasma. Results showed that 24 h after incubation, naked siRNA in plasma was almost completely degraded (FIG. 3B). On the contrary, (HA-S)-Ca-siRNA complexes retained their integrity and conferred complete resistance against plasma proteins and nuclease activity, suggesting their capability to serve as a stable carrier for systemic siRNA delivery.

Example 5

Cellular Uptake of siRNA Anionic Polyplexes

Figure 4A:
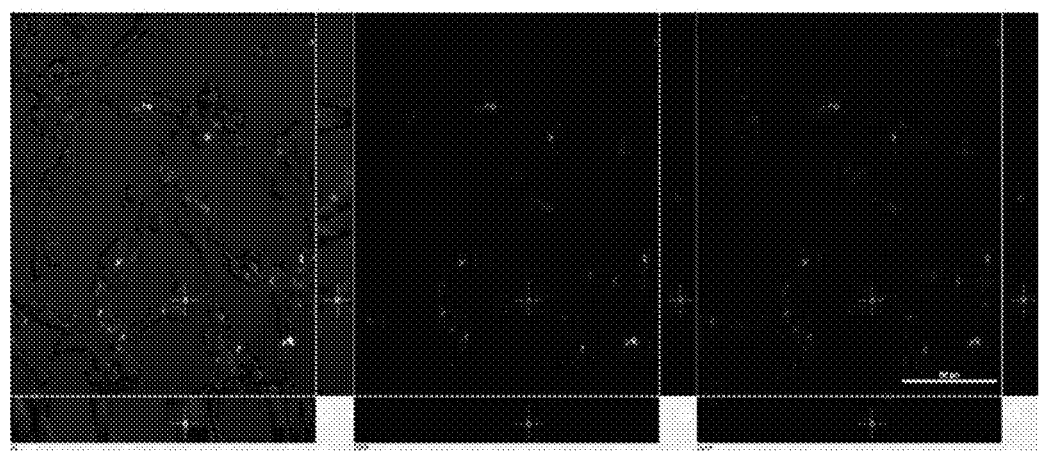
FIGS. 4A-4B show cellular uptake of siRNA anionic polyplexes in several cell types, visualized by laser scanning confocal microscope (LSCM). A. Uptake of (HA-S)-Ca-siRNA polyplexes in mouse colon carcinoma CT26 cell line, 1 h after addition in live cells (confocal image). Right panel: siRNA-Cy3 (red); Middle panel: 488 nm-HA-S (green); left panel—merged image. Cross point: representative intracellular co-localization event. B. Uptake of (HA-S)-Ca-siRNA polyplexes in primary mouse peritoneal macrophages, 3 h after addition in live cells. Top left panel: merged image; top right panel: 555 nm-HA-S (green); bottom left panel: siRNA-Cy5 (red), bottom right panel: bright field.
Figure 4B:
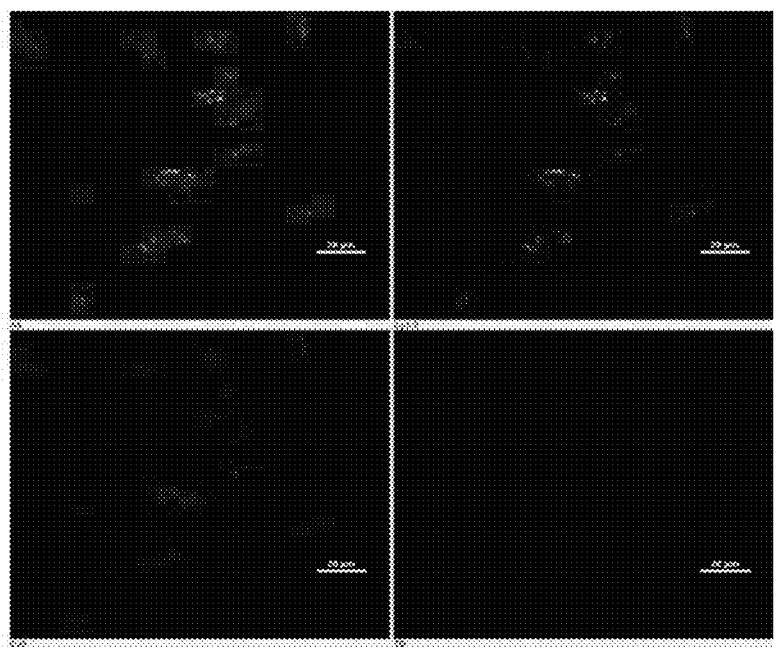

The uptake of siRNA ternary anionic polyplexes ((HA-S)-Ca-siRNA polyplexes) was examined in cell cultures of mouse colon carcinoma CT26 cell line and mouse primary peritoneal macrophages. Laser scanning confocal microscopy (LSCM) was used to identify entry into cells and accumulation in the cytoplasm. The results showed significant cellular uptake and accumulation of siRNA polyplexes in the cytoplasm (FIGS. 4A and 4B). Detailed 3D analysis confirmed the intracellular localization of the anionic polyplexes (FIG. 4A). Moreover, the results showed intracellular co-localization of siRNA and HA-S, further confirming the presence of both components in a single complex. Uptake results in primary macrophages showed cell entry and cytoplasmic accumulation of labeled siRNA anionic polyplexes (FIG. 4B).

Figure 5A:
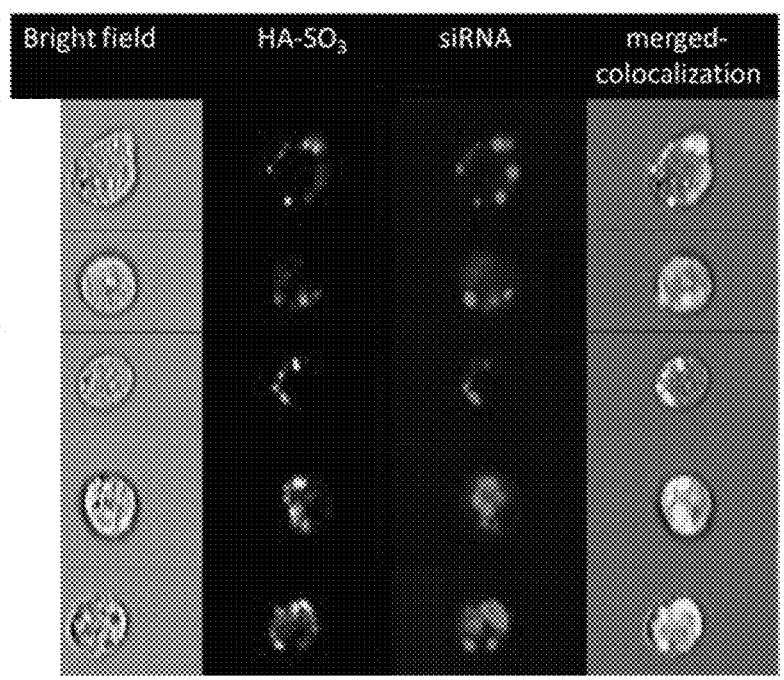
FIGS. 5A-5D show determination of the uptake of (HA-S)-Ca-siRNA polyplex by CT26 cells by imaging flow cytometry. A. Representative images captured by Amnis ImageStreamX flow cytometer of cells treated with (HA-S)-Ca-siRNA polyplexes for 2 h. First column shows bright field images, second column shows fluorescence images of HA-S labeled with 555-nm dye, third column shows fluorescence images of siRNA labeled with Cy5, and forth column shows florescence merged with b images of cells (co-localization of dyes). B. Cell population indicating single cells that have double positive (Cy3+Cy5+, upper pentagon) or double negative (Cy3–Cy5–, lower hexagon) fluorescence signals for Cy3 (HA-S) and Cy5 (siRNA). C. Bright Detail Similarity graph for Cy3+Cy5+ cells showing the degree of co-localization between Cy3 and Cy5. High colocalization (Bright Detail Similarity above 1) is observed along the black horizontal bar). D. Internalization score (IS) calculated by Amnis IDEAS software shows the level of internalization of Cy5 (the length of the red horizontal bar (left, lower bar, marked as R3) shows no internalization (scores less than 0), while the length of the black horizontal bar (higher, right horizontal bar, marked as R2) shows internalization (scores above 0; R2 is the region of interest for internalization score above 0; R3 is the region of no internalization)
Figure 5B:
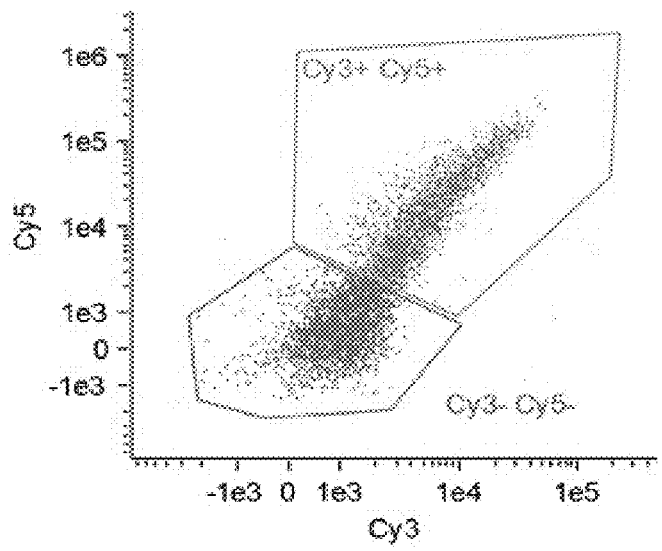
Figure 5C:
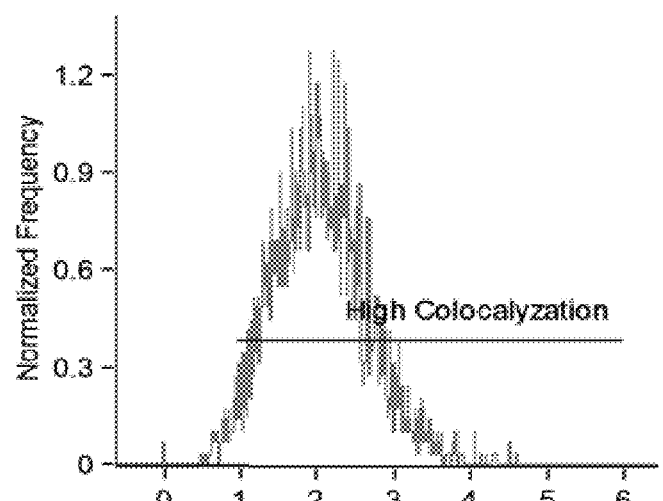
Figure 5D:
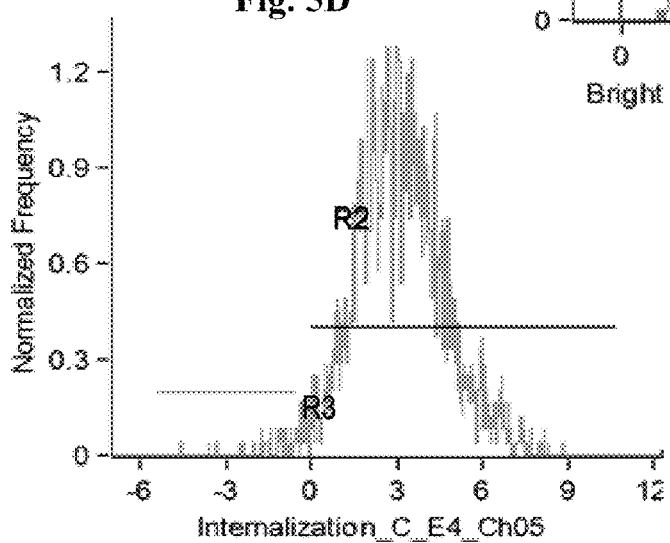

To further determine and quantify the uptake of (HA-S)-Ca-siRNA polyplexes by CT26 cells we used ImageStreamX, a powerful instrument that combines the statistical power, speed and sensitivity of flow cytometry with the powerful imaging of high resolution microscopy. The results showed cell entry of the polyplexes and accumulation in the cytoplasm (FIG. 5A) confirming the results obtained by confocal microscopy. In addition, results showed that uptake of anionic polyplexes occurred in 50% of cells as calculated by % of cells that showed positive signal of both HA-S and siRNA (FIG. 5B). Notably, analysis of co-localization of siRNA and HA-S (in cells that were positive to both probes) confirmed that most cells (97%) showed intracellular co-localization of both components (FIG. 5C). These results are in agreement with the results obtained by confocal microscopy and further confirm the presence of both components (siRNA and HA-S) in a single anionic polyplex. Analysis of siRNA internalization showed that the majority of cells (96%) had a positive value of internalization score (IS) indicating internalization of siRNA in these cells (FIG. 5D).

Example 6

The Effect of (HA-S)-Ca-siRNA Anionic Polyplexes on Cell Viability

Figure 6A:
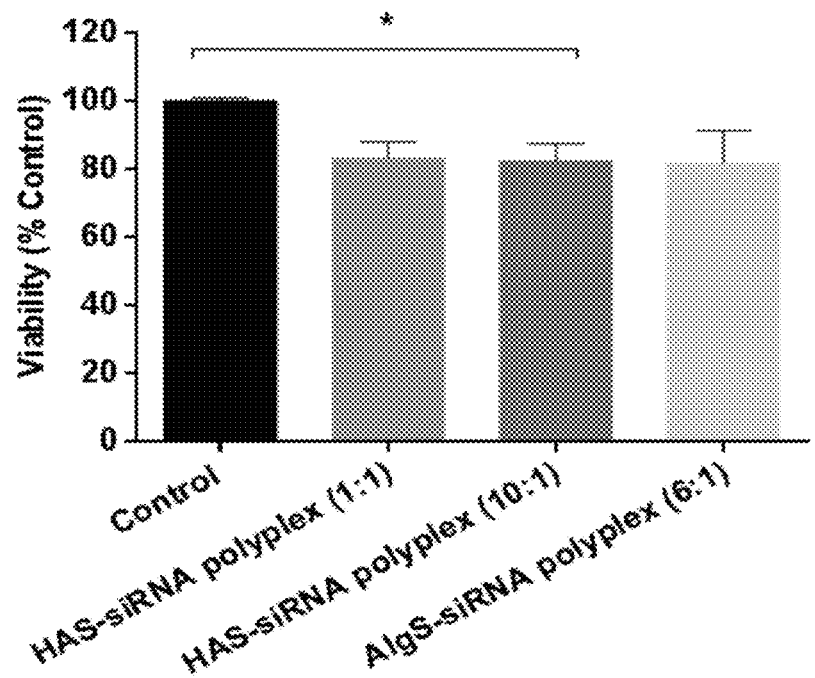
FIGS. 6A-6B shows cytocompatibility of (HA-S)-Ca-siRNA complexes. A. cell viability 72 hours after exposure of CT26 cells to various siRNA polyplexes. The results were normalized to untreated cells which were considered as 100% viable. Left to right: control; (HA-S)-Ca-siRNA polyplex (molar ratio of HA-S to siRNA is 1:1); (HA-S)-Ca-siRNA polyplex (molar ratio of HA-S to siRNA is 10:1); (Alg-S)-Ca-siRNA polyplex (ratio of Alg-S to siRNA is 6:1); *-p<0.05. B. Expression of several stress-related genes HMOX-1, HSP70 and Gcic, 24 h post-transfection with (left to right): control (untreated cells) (black bars), (HA-S)-Ca-siGFP (gray bars), (HA-S)-Ca-siNT (white bars), or lipofectamine (striped bars), evaluated by quantitative PCT (qPCR) and normalized to housekeeping gene (peptidylprolyl isomerase—PPIA) (compared to untreated control). *-p<0.05 (Dunnett's multiple comparisons test).
Figure 6B:
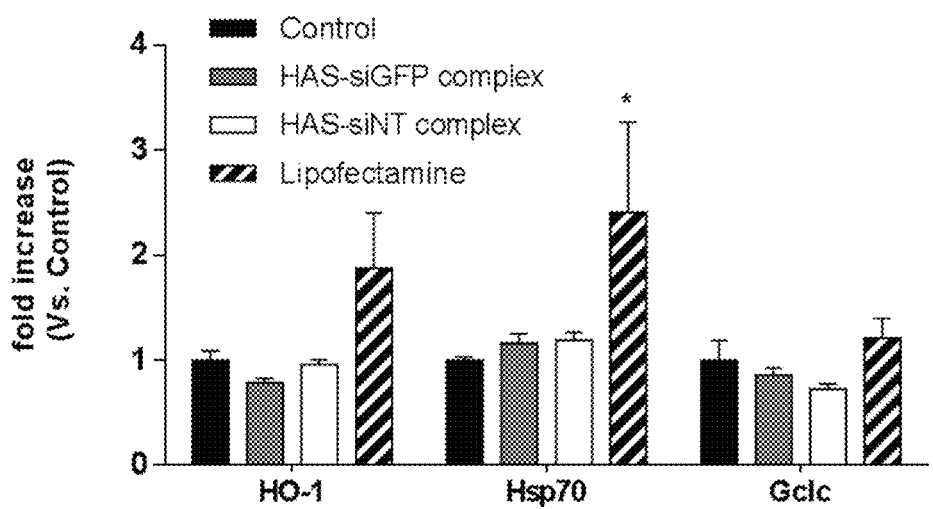

For assessing the effect of the anionic polyplexes on cell viability, PrestoBlue cell viability assay was utilized 72 h post transfection. As shown in FIG. 6A, the anionic polyplexes including eGFP siRNA had no significant negative impact on cell viability of CT26 cells, suggesting the cellular biocompatibility and safety of the anionic polyplex. Moreover, (HA-S)-Ca-siGFP or (HA-S)-Ca-siNT complexes did not induce the expression of several stress-related genes tested (HMOX-1, HSP70, and Gclc) (FIG. 6B), further confirming the cellular biocompatibility and safety of the proposed platform. Notably, lipofectamine induced a significant increase in HSP70 gene expression, compared to untreated control (p<0.05), and showed a trend of increased expression of other genes.

Example 7

Gene Silencing Studies

Figure 7A:
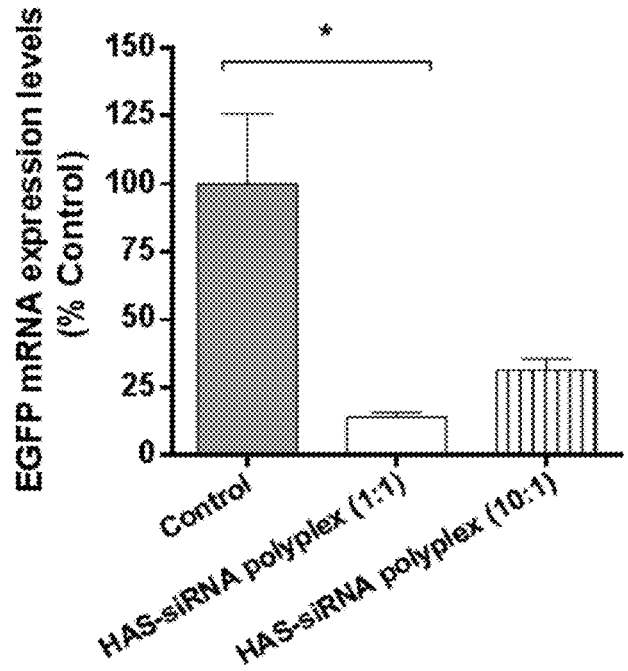
FIGS. 7A-7C show silencing efficiency of (HA-S)-Ca-siRNA polyplexes in eGFP (enhanced green fluorescent protein)-expressing CT26 cells. A. eGFP mRNA expression level analyzed by qPCR at 24 h post transfection after treatment with (HA-S)-Ca-siRNA polyplexes. Left to right: control; (HA-S)-Ca-siRNA siRNA polyplex (ratio of 1:1); (HA-S)-Ca-siRNA polyplex (ratio of 10:1). B. eGFP protein level analyzed by FACS at (left to right) 24 h (gray), 48 h (white), 72 h (black) post transfection with different anionic polyplexes (HA-S- and Alg-S-based). Left to right each set: control; (HA-S)-Ca-siRNA polyplex (ratio of HA-S to siRNA is 1:1); (HA-S)-Ca-siRNA polyplex (molar ratio of HA-S to siRNA is 10:1). (Alg-S)-Ca-siRNA polyplex (molar ratio of Alg-S to siRNA is 6:1); *-p<0.05. C. FACS analysis of eGFP expression after transfection with various anionic polyplexes prepared from unmodified HA or Alg of two molecular weights and at two molar ratios. P (interaction) <0.0001. All significant vs. untreated control (Dunnett's multiple comparisons test). Groups (left to right): HA (51 kDa)-Ca-siRNA polyplex (0.25:1), HA (51 kDa)-Ca-siRNA polyplex (2.5:1), HA (150 kDa)-Ca-siRNA polyplex (0.08:1), HA (150 kDa)-Ca-siRNA polyplex (0.8:1), Alg (30 kDa)-Ca-siRNA polyplex (0.4:1), Alg (30 kDa)-Ca-siRNA polyplex (4:1), Alg (100 kDa)-Ca-siRNA polyplex (0.1:1), Alg (100 kDa)-Ca-siRNA polyplex (1:1). In each group left to right: 24 h (gray), 48 h (white), 72 h (black).
Figure 7B:
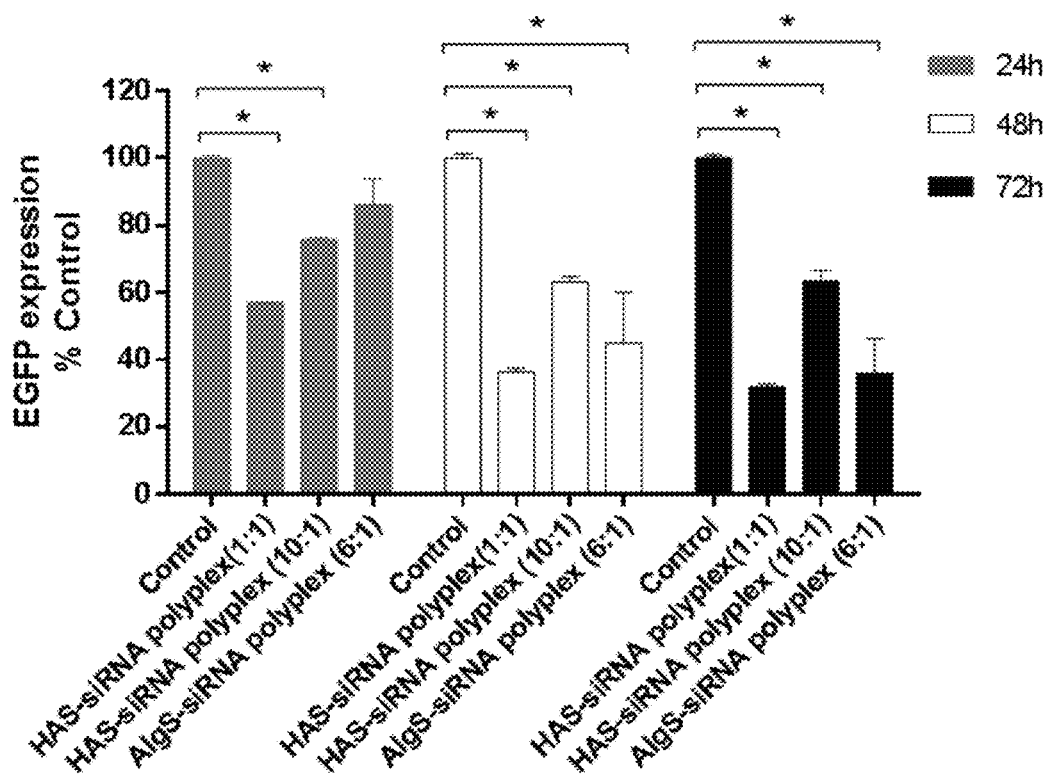

For examining the capability of ternary anionic polyplexes for delivering siRNA and inducing effective gene silencing, we first used siRNA against eGFP for investigating the silencing efficacy in eGFP-expressing CT26 cells, as a model system (FIG. 7). Analysis of silencing at the mRNA level was performed by qPCR analysis. Results showed a significant reduction in eGFP mRNA level by (HA-S)-Ca-siRNA polyplexes 24 h post transfection (FIG. 7A). A more prominent effect of 85% silencing was observed using the (HA-S)-Ca-siRNA polyplex formulation of 1:1 (HA-S: siRNA molar ratio). eGFP knockdown was also evaluated by measuring the protein level using FACS analysis at 24 h, 48 h, and 72 h post transfection. Results showed a significant reduction in eGFP expression level by (HA-S)-Ca-siRNA (1:1) polyplexes already after 24 h. Maximum reduction in eGFP expression level was observed after 72 h resulted in 70%, 40% and 65% silencing with (HA-S)-Ca-siRNA (1:1) polyplexes, (HA-S)-Ca-siRNA (10:1) polyplexes, and Alg-S-siRNA (6:1) polyplexes, respectively (FIG. 7B).

Figure 7C:
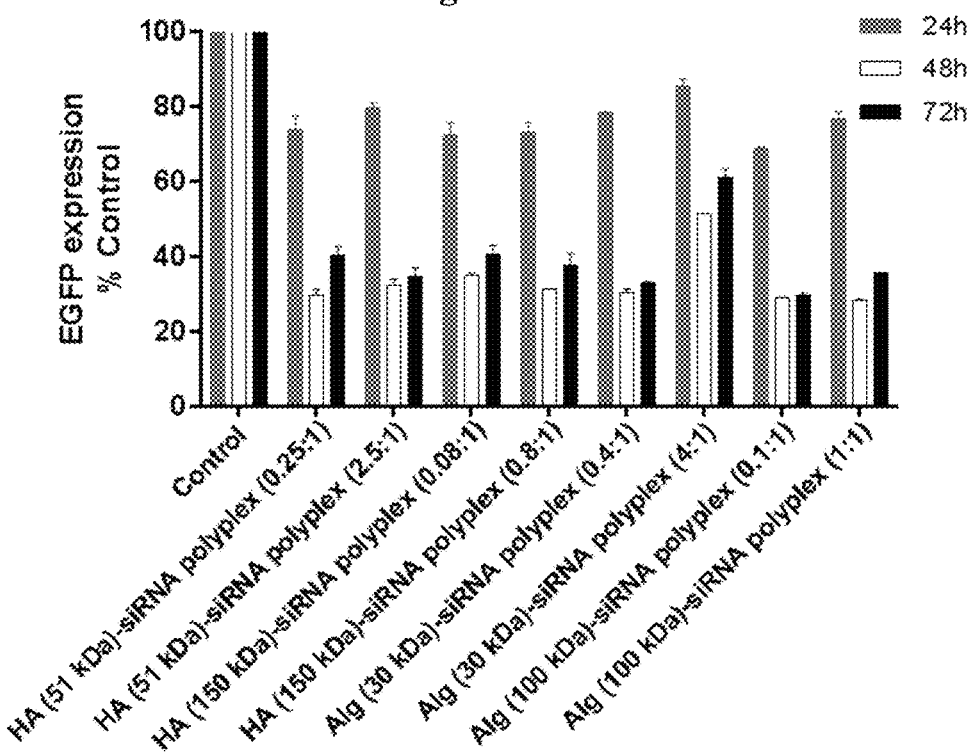

Silencing efficiency was also tested by measuring the eGFP protein level using FACS analysis at 24 h, 48 h, and 72 h post transfection with anionic polyplexes prepared with unmodified anionic polymers, HA and Alg. As seen in FIG. 7C, at molar ratios and molecular weight of each polymer tested, transfection with various anionic polyplexes resulted in significant reduction in eGFP expression level at 48 h and 72 h (~70% silencing in all conditions, except ~50% in Alg (30 kDa)-siRNA polyplex at 4:1 molar ratio).

Figure 8A:
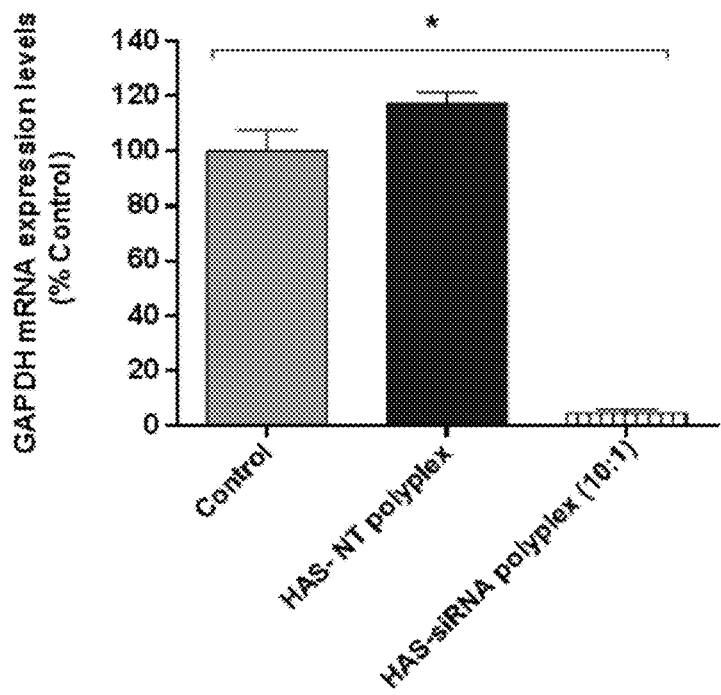
FIGS. 8A-8C show silencing efficiency of (HA-S)-Ca-siRNA polyplexes in various cell types, using anti-GAPDH (A, B) or anti-STAT3 (C) siRNAs. GAPDH mRNA expression levels were analyzed by qPCR at 24 h post transfection in Mouse embryonic fibroblasts (MEFs) (A) or in primary mouse peritoneal macrophages (B). Left to right: control, (HA-S)-Ca-siNT polyplex, (HA-S)-Ca-siRNA polyplex (10:1). NT: non-targeting siRNA. C. STAT3 mRNA expression level analyzed by qPCR at 24 h post transfection in human multiple myeloma U266 cells. Left to right: control, (HA-S)-Ca-siRNA polyplex (10:1). *-p<0.05.
Figure 8B:
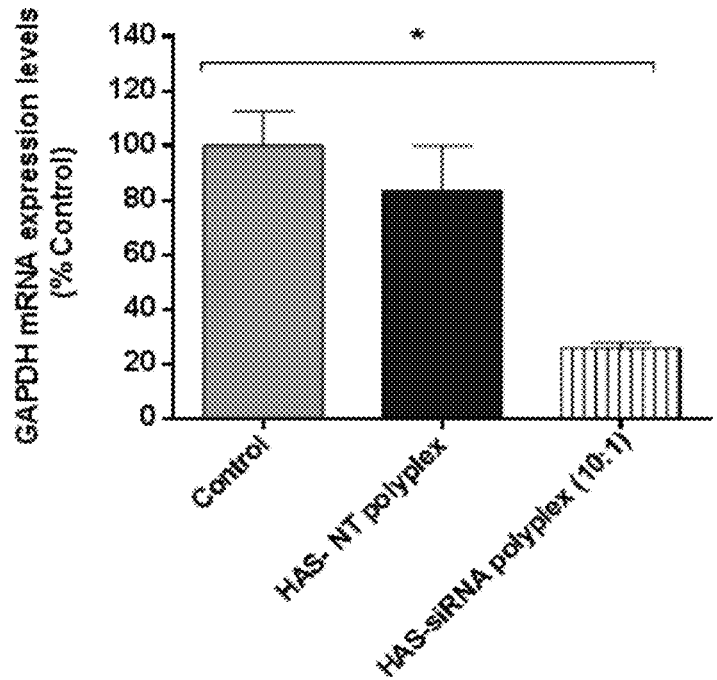

The efficacy of the anionic polyplexes as effective delivery system for nucleic acid therapeutic was proven for additional siRNAs in additional cell cultures. Mouse embryonic fibroblast (MEFs) and primary mouse peritoneal macrophages were treated with anionic polyplexes carrying siRNA against GAPDH and the mRNA expression level of GAPDH was analyzed by qPCR. Results showed a marked reduction in GAPDH mRNA expression level by (HA-S)-Ca-siRNA polyplexes with 95% and 75% silencing in MEFs and primary macrophages, respectively (FIGS. 8A and 8B). Same formulation of (HA-S)-Ca-siRNA polyplexes containing non-targeting siRNA was used in order to exclude a reduction in GAPDH mRNA levels by the polyplex itself. Results showed no difference in GAPDH mRNA levels by the non-targeting siRNA and therefore a non-specific effect by the transfection method was excluded.

Figure 8C:
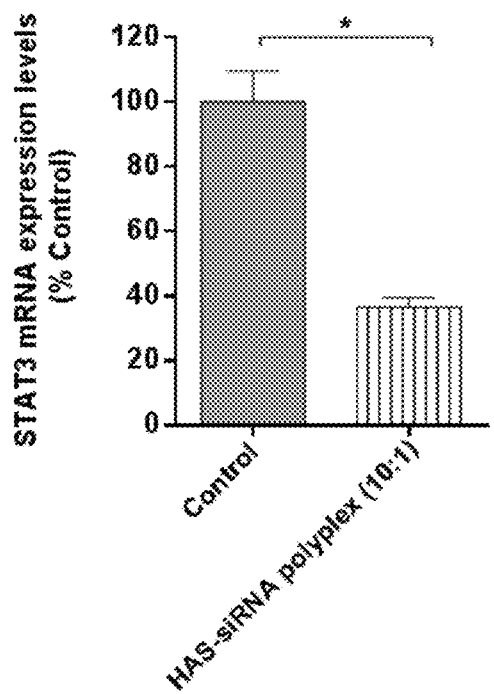

Additional silencing studies of a relevant therapeutic target (STAT3 transcription factor) were performed in a human cancer cell line multiple myeloma (U266). Results showed an effective silencing achieved by (HA-S)-Ca-siRNA polyplexes with 65% silencing in U266 cells (FIG. 8C).

Example 8

Regulation of Acute Inflammatory Response by STAT3 Silencing in Human Hepatocytes To investigate the therapeutic potential of (HA-S)-Ca-siRNA complexes, we selected STAT3 as a target gene in human hepatocyte HepG2 cell line as a clinically-relevant model for IL-6-induced acute phase response (APR, Brock et al., 2011). We used Dicer-substrate RNAs (DsiRNAs) for STAT3 targeting, which have increased potency in RNA interference compared to the traditional siRNAs (Rose and Behlke, 2008; Amarzguioui and Rossi, 2008).

Figure 9A:
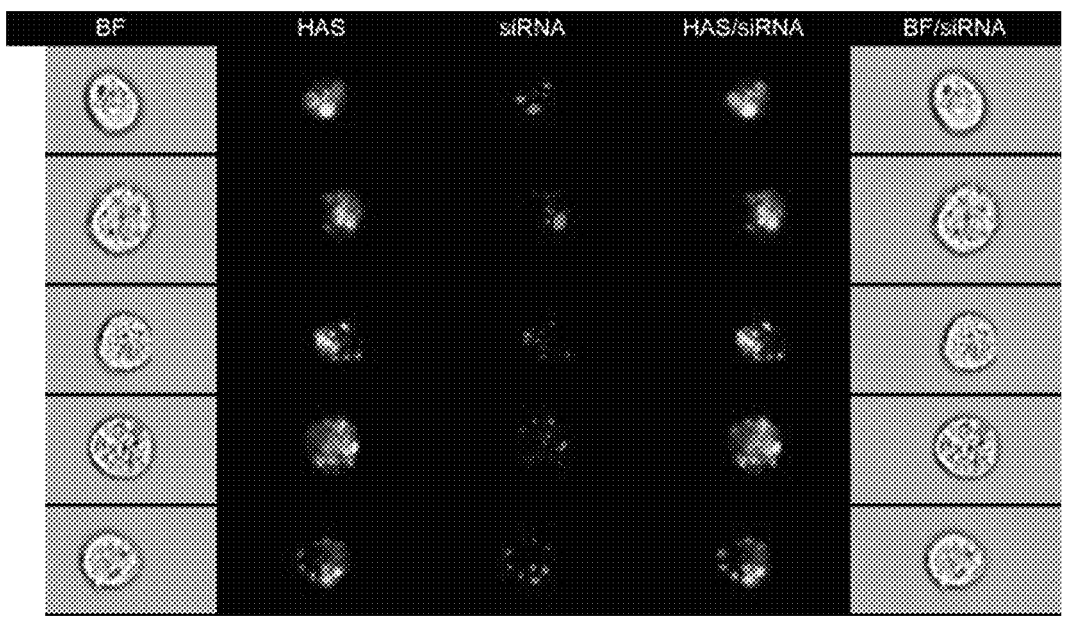
FIGS. 9A-9F show regulation of acute phase response (APR) in human HepG2 hepatocytes by STAT3 silencing with (HA-S)-Ca-siRNA complexes. (A) Representative cellular uptake images of (HA-S)-Ca-siRNA complexes in HepG2 cells captured by Amnis ImageStreamX flow cytometer. From left to right: bright field, HA-S (555 nm-labeled), siRNA (Cy5-labeled), (HA-S)-Ca-siRNA merged image), and merged image of bright field and siRNA fluorescence. (B) Internalization score (IS) showing the level of internalization of siRNA-Cy5, the length of black bar shows positive score (above 0) of internalization C. % of STAT3 silencing in HepG2 cells, mRNA levels of STAT3 were determined by qPCR and normalized to housekeeping gene (ACTB). Left to right: control, free siRNA, (HA-S)-Ca-siNT complex, (HA-S)-Ca-siSTAT3 complex, lipofectamine. P (one-way ANOVA)<0.0001. *-p<0.05 (Dunnet's multiple comparisons test), NT—non targeting siRNA, ND—not detectable. Western blotting (D) and densitometric analysis (E) of total and phosphorylated STAT3, with or w/o IL-6 stimulation. Cells were treated with (HA-S)-Ca-siSTAT3 complexes for 3 h, and then incubated for 48 h in culture medium prior to IL-6 addition (20 ng/mL) for 30 min. Band intensity was first normalized to GAPDH, and then to protein level in non-transfected unstimulated cells (total protein) or nontransfected stimulated cells (phosphorylated protein), taken as 100%. ND—not detectable. *-p<0.05 (Sidak's multiple comparisons test). In E left to right groups: STAT3 (gray), pSTAT3 (black). F qPCR analysis of known APR genes, serum amyloid A1 (SAA1) and fibrinogen, with or w/o IL-6 stimulation. Cells were treated with (HA-S)-Ca-siSTAT3 complexes for 3 h, and then incubated for 24 h in culture medium prior to IL-6 (20 ng/mL) addition for 24 h. mRNA levels of APR genes were determined by qPCR and normalized to housekeeping gene (ACTB). Component concentrations in all experiments: 50 nM (HA-S)/5 mM $Ca^{2+}$/50 nM siRNA. Left to right groups: SAA1 (black); fibrinogen (gray).
Figure 9B:
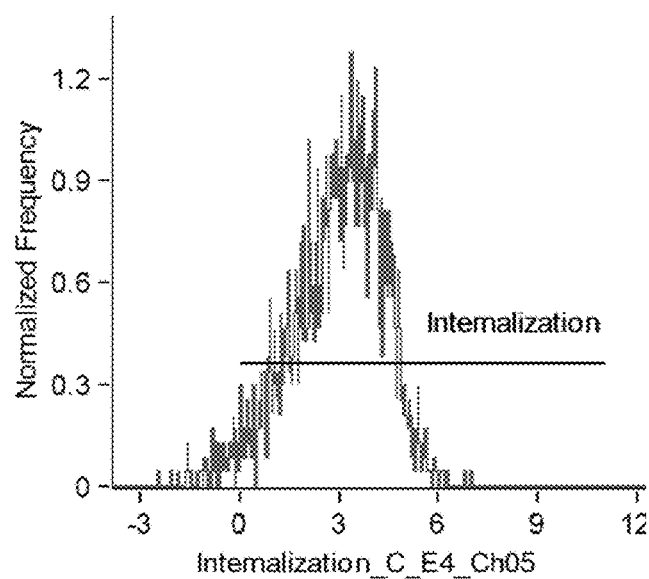
Figure 9C:
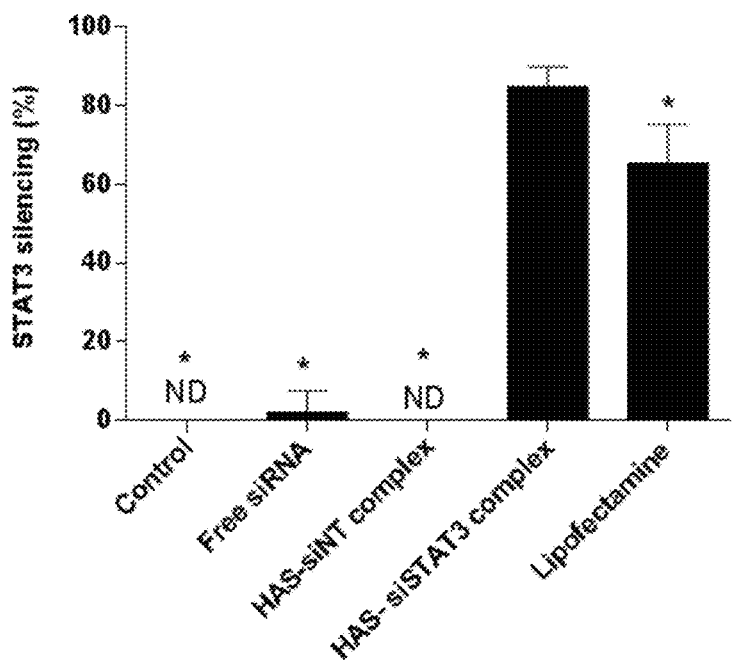

First, we analyzed the extent of cellular uptake of (HA-S)-Ca-siRNA complexes (a ratio of HA-S to siRNA or 1:1 and in the presence of 5 mM $Ca^{2+}$) in HepG2 cells by imaging flow cytometry using ImageStreamX instrument. The results demonstrated cellular entry of the complexes and accumulation in the cytoplasm (FIG. 9A). Quantitatively, the results showed that most of the cells (96%) had a positive value of internalization score (IS), indicating internalization and cytoplasmatic accumulation of siRNA in these cells (FIG. 9B). Next, we assessed the silencing efficiency of STAT3 by (HA-S)-Ca-siRNA complexes using qPCR, 24 h post-transfection. Results showed a significant (~85%) reduction in STAT3 mRNA level with HA-S/STAT3 siRNA (siSTAT3) complexes (FIG. 9C). No detectable effect was seen after the treatment with free siRNA or complexes bearing non-targeting siRNA (HAS-siNT) sequence. Notably, (HA-S)-Ca-siRNA complexes demonstrated more efficient silencing compared to lipofectamine (p<0.05).

Figure 9D:
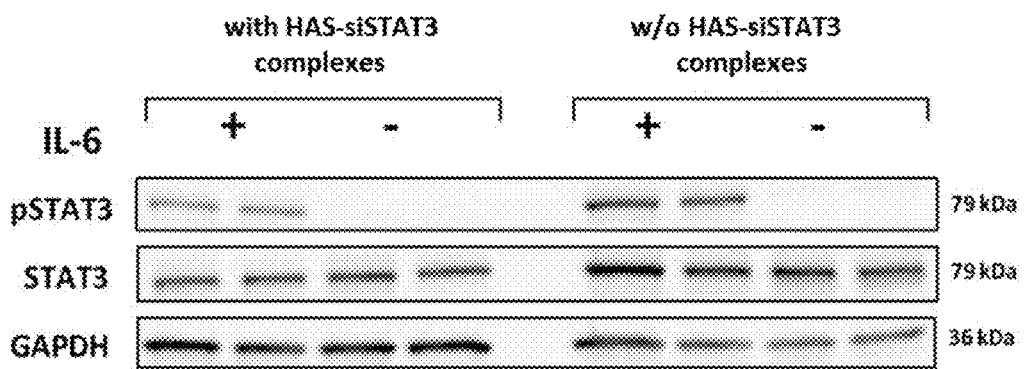
Figure 9E:
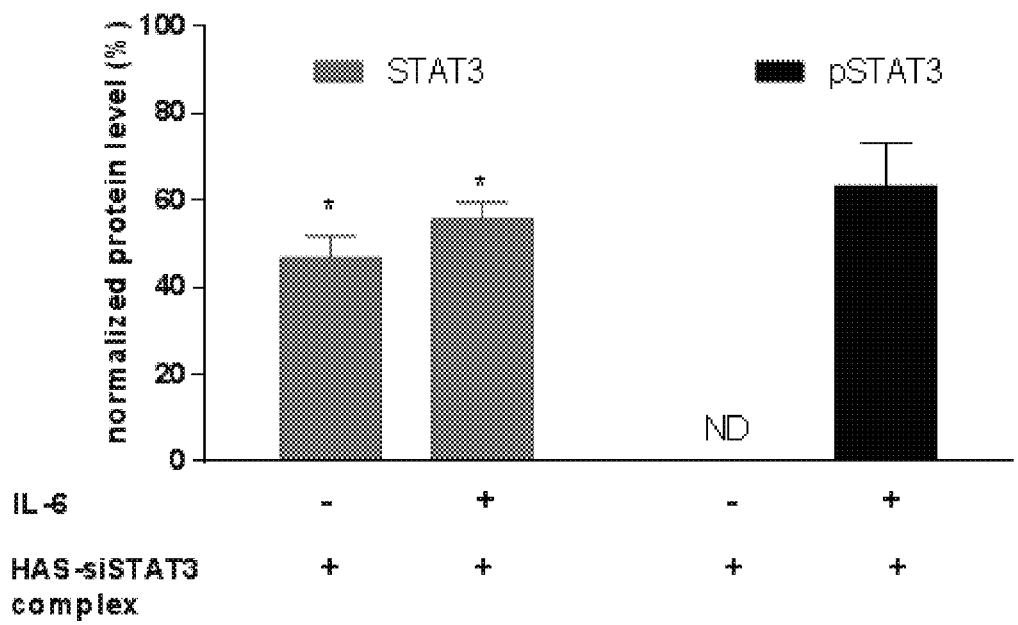
Figure 9F:
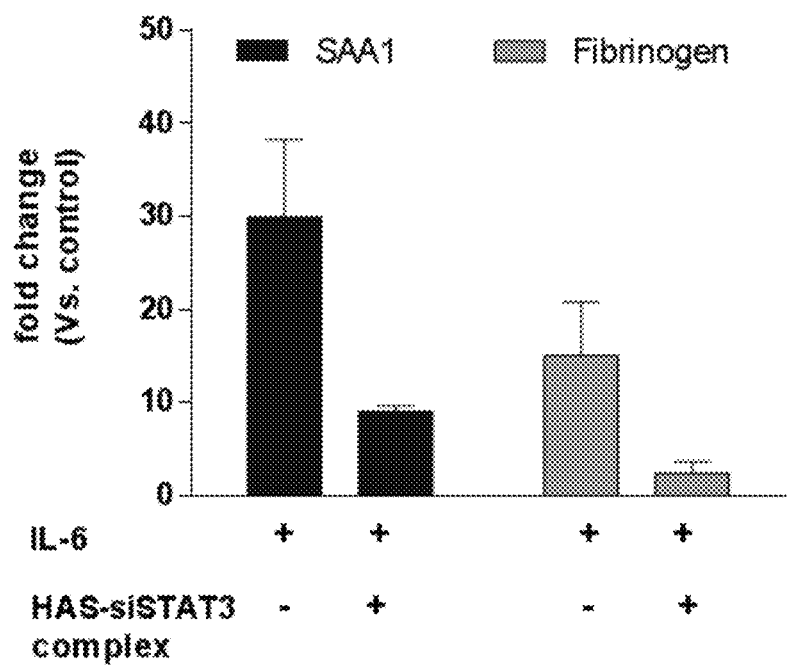

Finally, in order to assess the capability of (HA-S)-Ca-siSTAT3 complexes to repress APR, we performed a functional silencing study in HepG2 cells, under IL-6 stimulation. The STAT3 protein level and activation (phosphorylation on Tyr705) extent under various conditions was analyzed by Western immunoblotting. As shown in FIGS. 9D-9E, treatment with (HA-S)-Ca-siSTAT3 complexes reduced the STAT3 protein level by 2-fold, with and w/o IL-6 stimulation (p<0.05). Importantly, STAT3 silencing by (HA-S)-Ca-siSTAT3 complexes lead to reduction in the level of phosphorylated (active) form of STAT3 after IL-6 stimulation (~60% of protein level vs. non-transfected cells, p=0.14).

These results indicate that the silencing of STAT3 by (HA-S)-Ca-siSTAT3 complexes reduces the effect of IL-6 as a mediator of the APR. Therefore, we further tested the expression of known downstream APR-related genes, serum amyloid A1 (SAA1) and fibrinogen (FIG. 9F) (Nerstedt and Johansson, 2010; Asselin and Blais, 2011). Results showed IL-6-induced increase in expression levels of SAA1 and fibrinogen by 30-fold and 15-fold respectively, in non-transfected cells. Importantly, STAT3 silencing using (HA-S)-Ca-siSTAT3 complexes attenuated IL-6-induced elevation of SAA1 (by ~70%, p=0.13) and fibrinogen (by ~85%, p=0.16).

Example 9

Cellular Uptake of pDNA Complexes

Figure 10A:
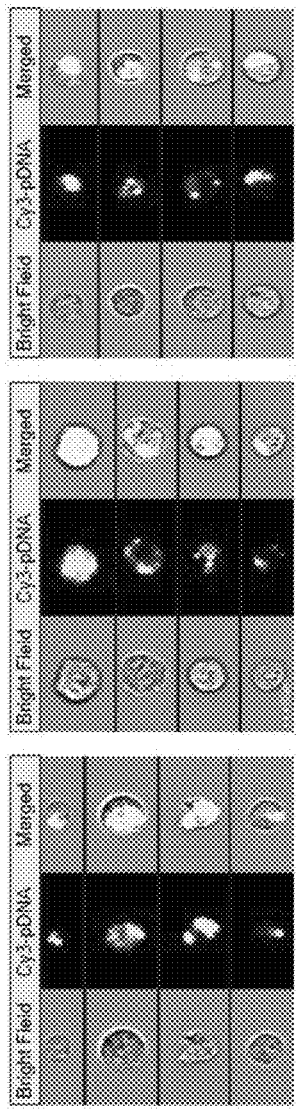
FIGS. 10A-10D show cellular uptake of plasmid DNA (pDNA) delivered via (HA-S)-Ca-pDNA complexes in CT26 cells and GFP (green fluorescent protein) expression in CT26 cells transfected with Alg-S- or HA-S-Ca-plasmid GFP DNA (pGFP) polyplexes by imaging flow cytometry. A. Representative ImageStreamX images of CT26 cells successfully transfected with Cy3-labeled pDNA complexes. B. Imaging flow cytometry analysis of Cy3-labeled pDNA complex uptake in CT26 cells. Successful uptake was defined by a fluorescence intensity of at least 1E04 A.U. Left to right panels represent: cells transfected with (HA-S)-Ca-pDNA (26.3% cell uptake); cells transfected with naked plasmid (0.83% cell uptake), and untransfected cells. Representative images captured by Amnis ImageStreamX flow cytometer of cells treated with (Alg-S)-Ca-pGFP polyplexes (C) or (HA-S)-Ca-pGFP polyplexes (D). for 4 h, followed by 48 h incubation. First column shows bright field images, second column shows fluorescence images of expressed GFP. Each row represents a treated cell.
Figure 10B:
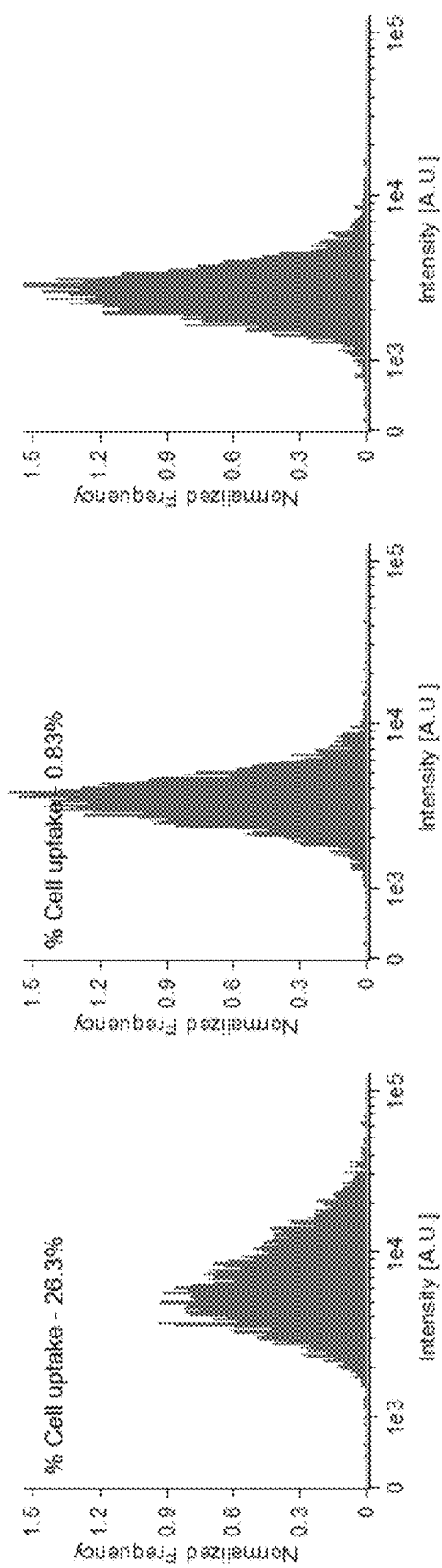

The visualization and quantification of pEGFP entry to CT26 cells was performed by imaging flow cytometry using ImageStreamX instrument. FIG. 10A shows representative images of cellular entry of the ternary complexes and accumulation in the cytoplasm. As can be seen in FIG. 10B, 26.3% of the cells showed cellular uptake of HA-S/pDNA complexes, compared to 0.83% for naked pDNA, which corresponds to an increase by two orders of magnitude.

Figure 10C:
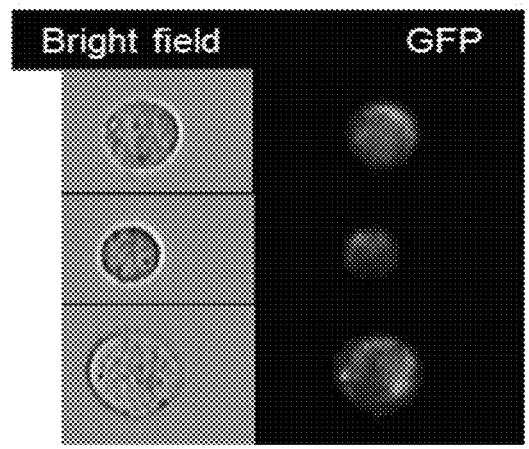
Figure 10D:
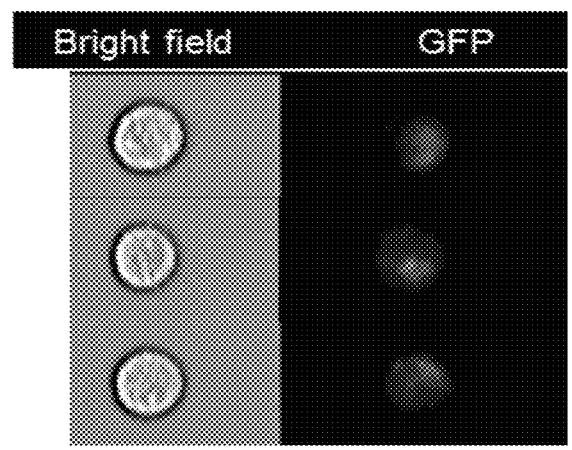

The capability of the anionic polyplexes to deliver plasmid DNA (pDNA) into cell nucleus and induce effective gene expression, was examined by following pDNA driving eGFP expression in CT26 cells, as a model system (FIGS. 10C-10D). Imaging flow cytometry using ImagestreamX instrument showed effective GFP expression 48 h after transfection, using Alg-S (FIG. 10C) and HA-S-(FIG. 10D) based polyplexes.

Example 10

Physical Characterization of Binary Divalent Cation-siRNA Complexes

Atomic force microscopy (AFM) and transmission electron microscopy (TEM, using gold-labeled siRNA) showed that Ca2$^+$-siRNA complexes (lacking an anionic polymer) form nanoparticles of a similar diameter size (78.9±20.1 nm, n=254, and 70. AFM and TEM, respectively). Moreover, DLS and zeta potential measurements confirmed the formation of nano-sized complexes of 84.5±7.7 nm in diameter, with surface charge of calcium-siRNA complexes −6.7±0.7 mV, for 5 mM/50 nM calcium-siRNA complexes (data not shown).

As determined by EtBr exclusion assay, at calcium concentrations of 50-200 mM, stable Ca2$^+$-siRNA complexes were obtained with a molar ratio of 8×10$^4$ of Ca$^{2+}$:siRNA and greater. As to the stability of the complex, following 24 h incubation, the presence of serum or possible competition with increasing amounts of heparin, at 2:1 and 5:1 w/w ratios to siRNA, did not affect complex integrity and did not result in significant siRNA release. Furthermore, after 3 hrs incubation with RNase A, siRNA was recovered from the complexes using cation-exchange resin, while naked siRNA was completely degraded. The recovery percentage of siRNA from the complexes was similar to untreated complexes (data not shown).

Example 11

Biological Effect of Ca-siRNA Complexes

To evaluate the capability of Ca$^{2+}$-siRNA complexes to deliver siRNA into the cytoplasm and induce effective gene silencing, we used siRNA targeted against eGFP in eGFP-expressing CT26 cells as a model system. Flow cytometry analysis results of eGFP expression (protein level) following treatment with various siRNA formulations at 24, 48 and 72 hrs post-transfection showed that at 72 hrs, using 4 or 5 mM calcium at constant siRNA concentration (50 nM), high (~80%) level of silencing was achieved (p>0.05 vs. lipofectamine) (FIG. 11A).

A decrease in calcium concentration was associated with a significant reduction (at 3 mM) or complete loss of (1 and 2.5 mM) of the silencing effect at the protein level. Moreover, at a constant calcium concentration (5 mM), maximal silencing was achieved using 50 nM siRNA. Lower siRNA concentrations did not induce silencing, when transfected using calcium complexes or lipofectamine (FIG. 11B).

Figure 12A:
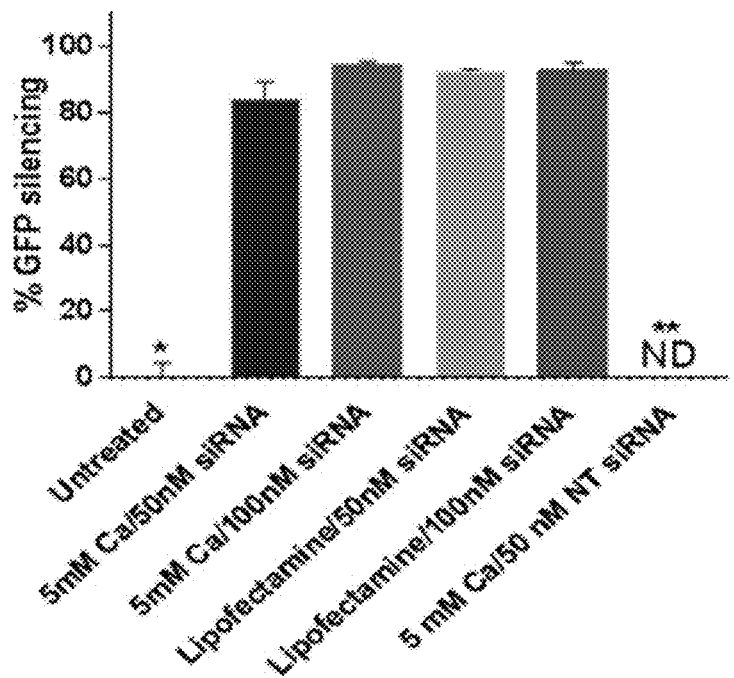
FIGS. 12A-12C show silencing efficiency of $Ca^{2+}$-siRNA complexes in various cell types at the mRNA level, by qPCR. A. eGFP silencing at 24 h post-transfection in eGFP-CT26 cells. Left to right: untreated; 5 mM $Ca^{2+}$/50 nM siRNA; 5 mM $Ca^{2+}$/100 nM siRNA; Lipofectamine/50 nM siRNA; Lipofectamine/100 nM siRNA; 5 mM $Ca^{2+}$/50 nM NT siRNA. p (one-way ANOVA) b 0.0001. *p b 0.05 (Tukey's multiple comparisons test vs. all groups except NT siRNA group); **p b 0.05 (Tukey's multiple comparisons test vs. all groups except untreated group). B. GAPDH silencing at 24 h post-transfection in MEFs. Left to right: untreated; 5 mM $Ca^{2+}$/50 nM NT siRNA; 3 mM $Ca^{2+}$/50 nM SIRNA; 4 mM $Ca^{2+}$/50 nM siRNA; 5 mM $Ca^{2+}$/50 nM siRNA. p (one-way ANOVA) b 0.0001. *p b 0.05 (Tukey's multiple comparisons test). C. GAPDH silencing at 24 h post-transfection in primary mouse peritoneal macrophages. Left to right: Untreated; 5 mM $Ca^{2+}$/50 nM NT siRNA; 5 mM $Ca^{2+}$/50 nM siRNA. p (one-way ANOVA)=0.008. *p b 0.05 (Dunnett's multiple comparisons test).
Figure 12B:
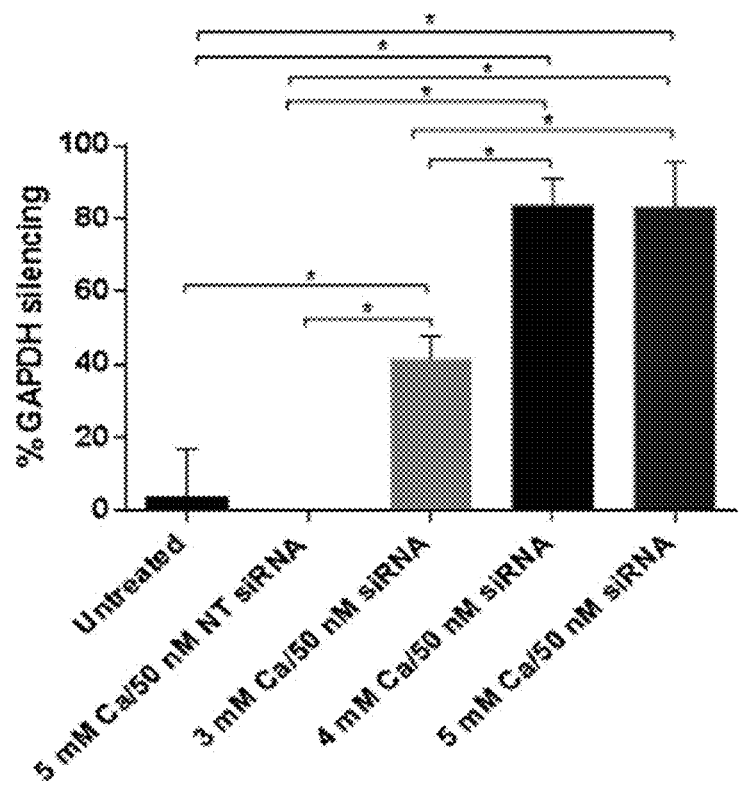
Figure 12C:
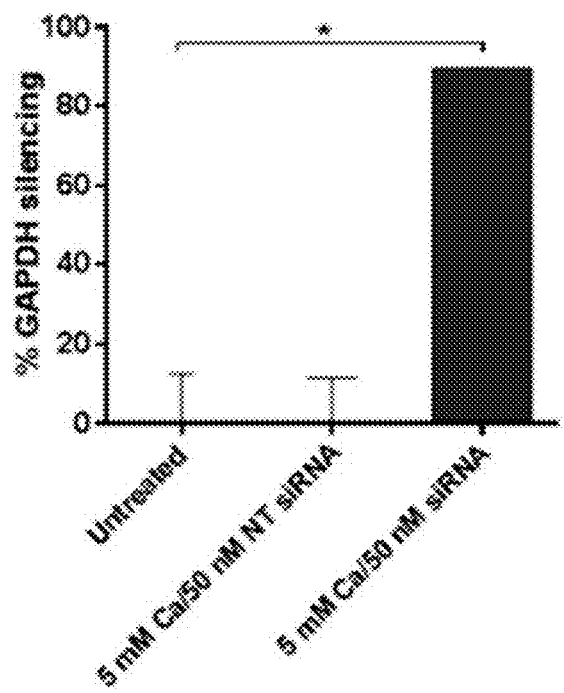
Figure 13A:
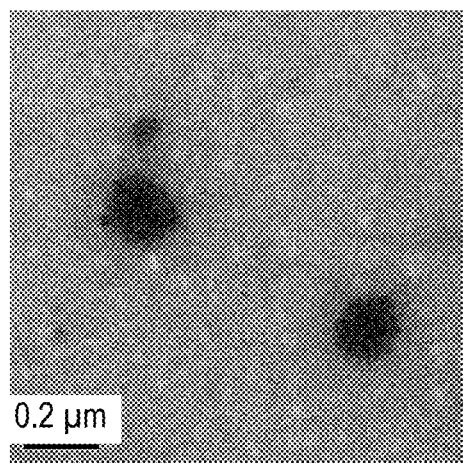
FIGS. 13A-13D show TEM images of binary cation-siRNA complexes. A. $Ca^{2+}$-siRNA. B. $Mg^{2+}$-siRNA. C. $Mn^{2+}$-siRNA. D. $Ba^{2+}$-siRNA.
Figure 13B:
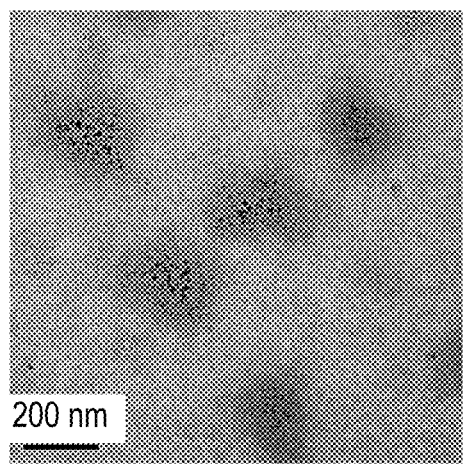
Figure 13C:
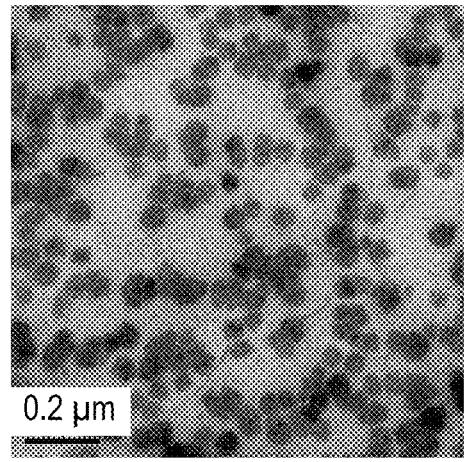
Figure 13D:
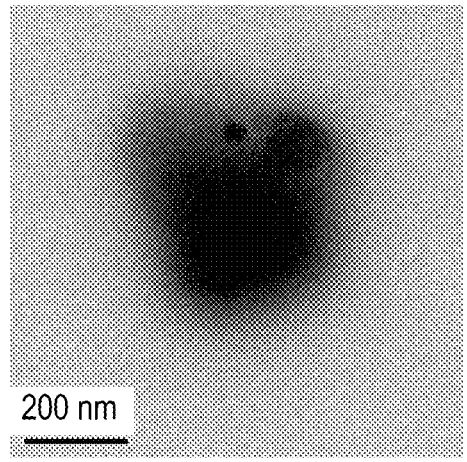

Effective gene silencing was also confirmed at mRNA level using qPCR analysis. Results showed a significant (~90%) reduction in eGFP mRNA levels by Ca$^{2+}$-siRNA complexes 24 hrs post transfection (FIG. 12A). Mouse embryonic fibroblasts (MEFs) and primary mouse peritoneal macrophages were treated with calcium complexes including siRNA against GAPDH, and the mRNA level of this gene was analyzed by qPCR. Results showed a marked reduction in GAPDH mRNA expression level induced by Ca$^{2+}$-siRNA complexes, with ~85% silencing in MEFs and primary macrophages (5 mM calcium), compared with untreated cells. A possible non-specific gene silencing effect of Ca2$^+$-siRNA complexes was excluded using a non-targeting siRNA sequence, resulting in no difference in target mRNA levels compared to untreated control (FIGS. 12B, C).

Example 12

Complexation of siRNA with Different Di-valent Cations

The formation of nanocomplexes between siRNA and divalent cations other than Ca$^{2+}$, such as Mg$^{2+}$, Mn$^{2+}$, Ba$^{2+}$, and Zn$^{2+}$ was studied and the nanocomplex physical features were compared to those of the Ca$^{2+}$-siRNA complexes. TEM images reveal that all tested divalent cations yielded nanocomplexes upon interaction with siRNA. The nanocomplexes had a spherical shape, similar to the shape of Ca$^{2+}$-siRNA complexes and their dry size was at the same order of magnitude (FIG. 13). By DLS, the average size of the nanocomplexes was the same order of magnitude as that of Ca$^{2+}$-siRNA, ~100 nm in diameter (Table 5) excluding the nanocomplex of Mn$^{2+}$-siRNA, which showed 50% greater size compared to Ca$^{2+}$-siRNA nanocomplex. Zeta potential analysis revealed that the nanocomplexes of Mg$^{2+}$, Mn$^{2+}$, Ba$^{2+}$, but not of Zn$^2$, displayed slightly negative surface charge, in the range of ~−8.2-(−12 mV), at the same range as the Ca$^{2+}$-siRNA nanocomplex (Table 5). The size and surface charge of the nanocomplexes kept stable for 24 h, indicating their stability as colloid suspensions.

TABLE 5

Characterization of binary complexes formation from different divalent cations

| Cation | Diameter (nm) | | | ζ potential (mV) | | | Encapsulation (%) |
|---|---|---|---|---|---|---|---|
| | 0 hr | 3 hr | 24 hr | 0 hr | 3 hr | 24 hr | 0 hr |
| $Ca^{2+}$ | 99.6 ± 25.3 | 110.5 ± 18.4 | 115.6 ± 12.9 | −11.6 ± −1.7 | −11.9 ± −0.7 | −11.9 ± −0.9 | 96.8 ± 0.5 |
| $Mg^{2+}$ | 91.0 ± 16.0 | 97.9 ± 19.3 | 122.3 ± 7.5 | −12.0 ± −1.3 | −13.0 ± −1.4 | −13.1 ± −0.7 | 95.6 ± 0.1 |
| $Mn^{2+}$ | 156.6 ± 54.8 | 157.4 ± 22.6 | 168.0 ± 38.8 | −8.1 ± −0.5 | −6.2 ± −0.7 | −6.2 ± −1.5 | 97.0 ± 0.2 |
| $Ba^{2+}$ | 103.2 ± 38.3 | 117.4 ± 15.3 | 116.3 ± 9.3 | −9.3 ± −0.9 | −10.1 ± −0.5 | −9.8 ± −2.1 | 96.7 ± 0.3 |
| $Zn^{2+}$ | 95.1 ± 19.0 | — | — | 21.1 ± −3.3 | — | — | 98.0 ± 0.2 |

Particles include 5 mM cation and 50 nM siRNA; Results are ± STD (n = 5);

Effective complexation was attained for a molar ratio of $10^4$ to 1 of the bivalent cation and siRNA. The entrapment efficiency, measured by the Ribogreen exclusion assay (Table 5) and by EtBr exclusion assay (data not shown), was ~96% of the input siRNA for all tested nanocomplexes, very similar to the value obtained for the $Ca^{2+}$-siRNA nanocomplex.

Figure 14A:
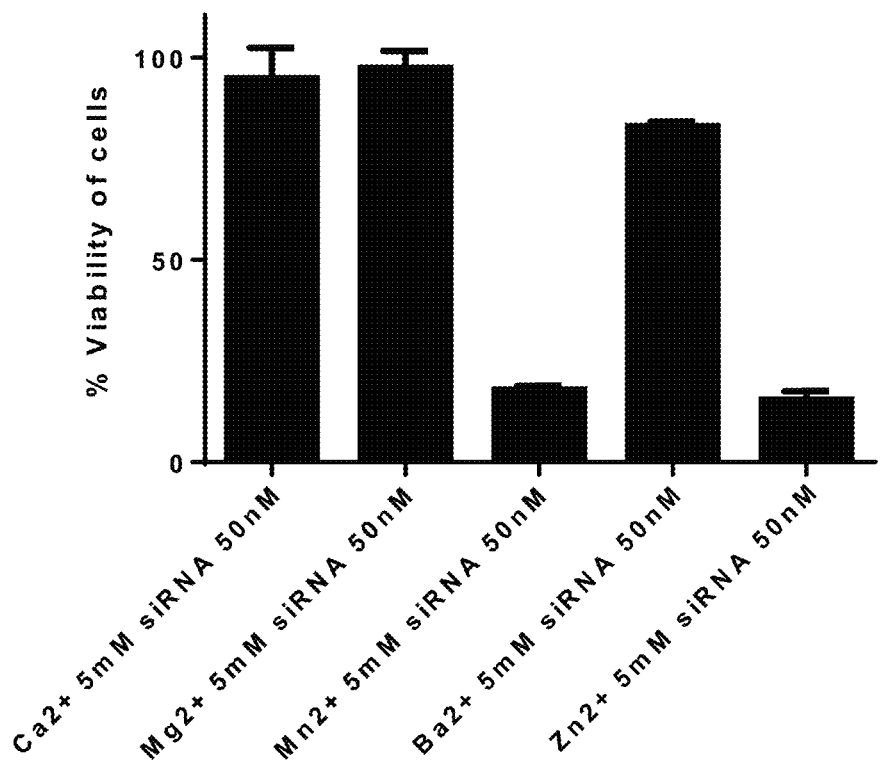
FIGS. 14A-14B show the effect of binary cation-siRNA complexes on cell viability. % Viability of eGFP-expressing CT26 cells (±SEM) was measured after treatment for 3 hours with nano-complexes, 24 hours after transfection, using PrestoBlue® assay after 1 hour incubation. A. 5 mM cation concentration, 50 nM siRNA concentration. B. Physiological concentrations of cations ($Ca^{2+}$—5 mM, $Mg^{2+}$—2.5 mM, $Mn^{2+}$—0.45 µM, $Ba^{2+}$—1.5 µM, $Zn^{2+}$—0.035 µM). From left to right: $Ca^{2+}$, $Mg^{2+}$, $Mn^{2+}$, $Ba^{2+}$, $Zn^{2+}$.
Figure 14B:
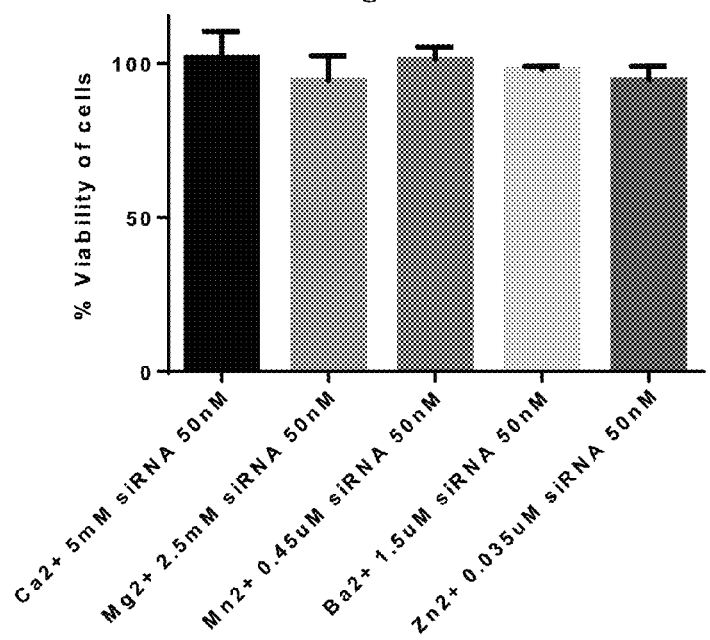

The cytocompatibility of the different nanocomplexes was followed by measuring the cell viability for 24 h in cultures of eGFP-expressing CT26 cells after their exposure to the nanocomplexes (FIG. 14). Of the nanocomplexes tested, $Mn^{2+}$-siRNA and $Zn^{2+}$-siRNA nanocomplexes were the most cytotoxic to cells (15% survival after 24 h) while $Ba^{2+}$-siRNA and $Mg^{2+}$-siRNA nanocomplexes were cytocompatible similar to the $Ca^{2+}$-siRNA nanocomplexes.

Based on the above results, $Mg^{2+}$-siRNA and $Ba^{2+}$-siRNA nanocomplexes were chosen for cell uptake and gene silencing studies in order to elucidate the mechanism of $Ca^{2+}$-siRNA nanocomplex.

Example 13

Cell Uptake and Gene Silencing

Figure 15A:
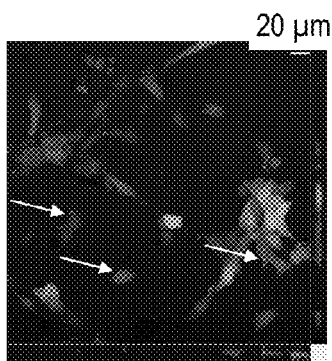
FIGS. 15A-15E show cellular uptake and silencing studies of binary cation-siRNA complexes. Cellular uptake (A-D) and silencing effect (E) of binary complexes with different cations; A. $Ca^{2+}$-siRNA. B. $Mg^{2+}$-siRNA. C. $Ba^{2+}$-siRNA. Green: CT26 cells; blue: nucleus; red: Cy3-labeled siRNA. D. % of cells transfected after 3 hr. E. Silencing effect on eGFP CT26 cells of different nano-complexes. Left to right groups: $Ca^{2+}$, $Mg^{2+}$, $Ba^{2+}$; left to right each group: 24 hours, 48 hours, 72 hours. Results are ±SEM (n=3).
Figure 15B:
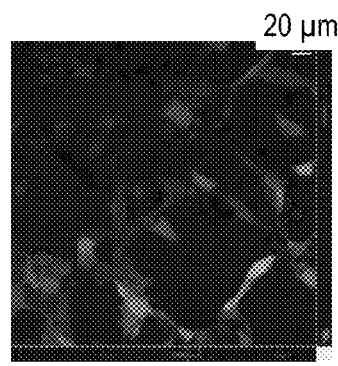
Figure 15C:
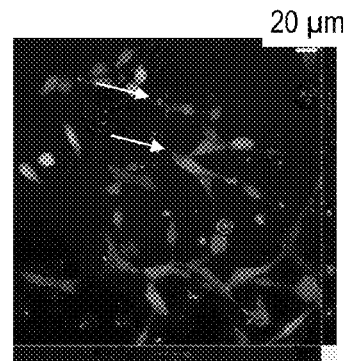

Using Cy3-labeled siRNA (red) and confocal microscopy, we examined whether the $Mg^{2+}$-siRNA and $Ba^{2+}$-siRNA nanocomplexes are efficiently taken up by the eGFP-transfected CT26 cells (green). FIG. 15A presents cell uptake of $Ca^{2+}$ siRNA nanocomplex; the red nanocomplexes are seen scattered in the cells (arrows), at the same plane as the nucleus (blue, marked by an orange cross on the XZ and YZ planes). By contrast, $Mg^{2+}$-siRNA nanocomplexes were not taken up by the cells (FIG. 15B). $Ba^{2+}$-siRNA nanocomplexes were found to precipitate in cell medium, in proximity to the cell membrane (arrows, as seen by the orange cross not lining with the cytoplasm in the XZ and YZ planes) (FIG. 15C); no measurable siRNA was detected in the cell cytoplasm by this analysis.

Figure 15D:
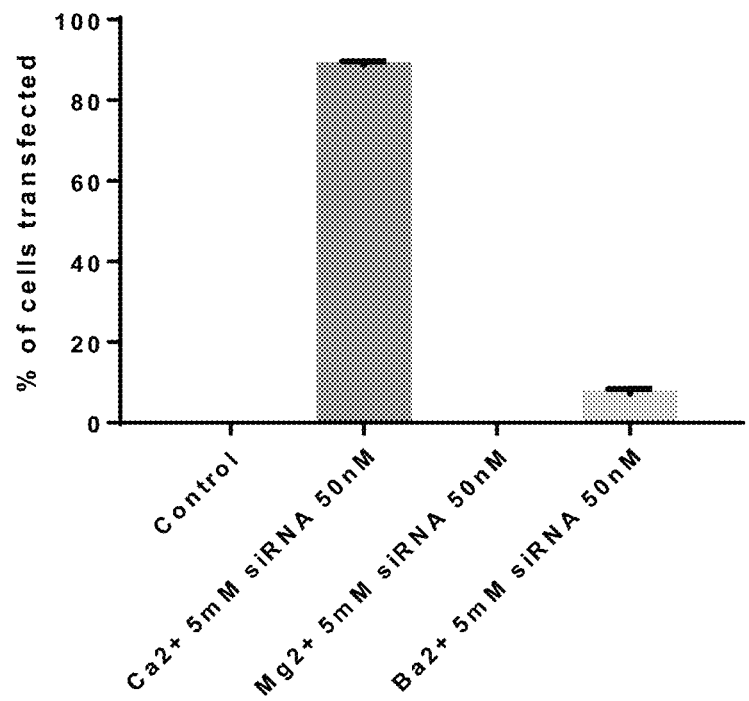

Quantitatively, cell uptake of the nanocomplexes was determined using the ImageStreamX imaging flow cytometry device; a powerful instrument that combines the statistical power, speed and sensitivity of flow cytometry with imaging capabilities of high-resolution microscopy. Cy-5 labeled siRNA nanocomplexes created with $Ba^{2+}$, $Mg^{2+}$ or $Ca^{2+}$, were added to monolayers of CT26 cells and the analysis performed 3 h later. More than 90% of the cells showed uptake of $Ca^{2+}$-(Cy5-siRNA) nanocomplex compared with only 9% in the case of $Ba^{2+}$-siRNA and none for $Mg^{2+}$-siRNA nanocomplexes (FIG. 15D).

Figure 15E:
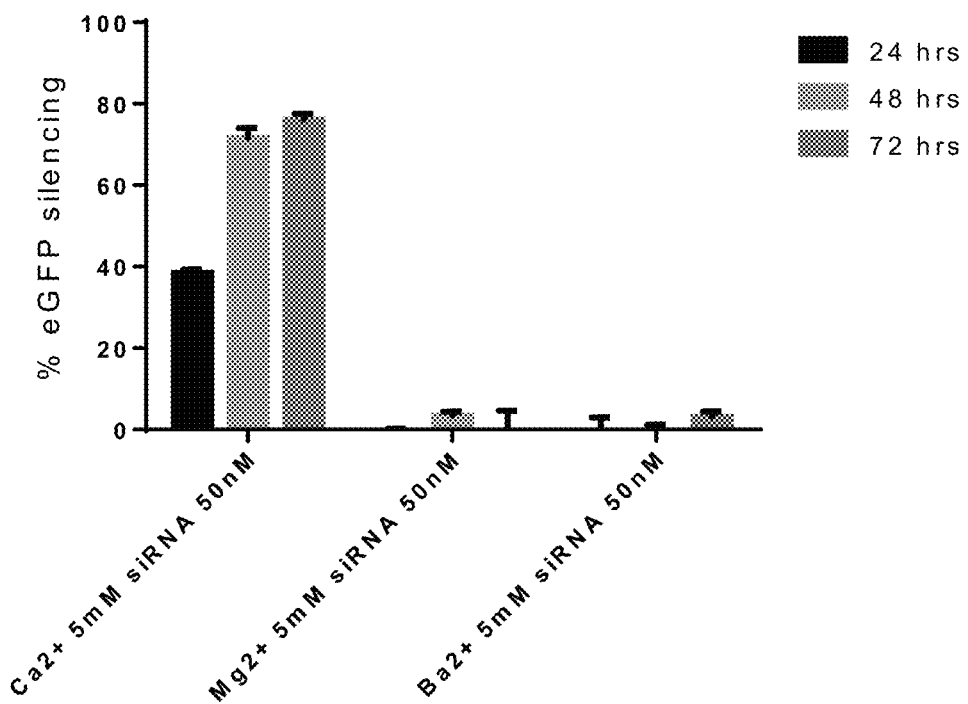

EGFP silencing in eGFP-expressing CT26 cells was studied for the three nanocomplexes entrapping eGFP siRNA by FACS. The most effective eGFP gene silencing (>80%, 72 h post transfection) was achieved with the $Ca^{2+}$ siRNA nanocomplex, while the nanocomplexes of $Ba^{2+}$-siRNA (~9% silencing) and $Mg^{2+}$-siRNA (0%) were ineffective (FIG. 15E).

Example 14

Kinetics of Nanocomplex Uptake and Accumulation in Cells

Cell uptake kinetics of the $Ca^{2+}$-siRNA nanocomplexes and their accumulation in cytosol were followed over time, using the ImageStreamX imaging flow cytometry device. FIG. 16A represents a series of representative cell images that have taken up the fluorescent-labeled nanocomplexes, 3 h post transfection; the nanocomplexes appear to be located in defined areas suggesting they reside in endosomes. The percentage of cells taking up the complexes increased with transfection time; the greatest percentage of transfected cells, 85%, was achieved after 6 h of transfection and they contained at least a single endosome with nanocomplexes (FIG. 16B). Per cell, the mean fluorescence intensity (MFI) increased with time up to 6 h post initiation of the experiment and then the MFI per cell decreased, indicating siRNA elimination/degradation over time (FIG. 16C).

Example 15

Effect of Inhibitors on Cellular Uptake

To elucidate the endocytic pathways involved in the uptake of $Ca^{2+}$-siRNA nanocomplexes, we employed a number of inhibitors that are specific to these pathways: PitStop2® to inhibit clathrin mediated endocytosis, Dynasore to inhibit dynamin mediated endocytosis, and Genistein to inhibit caveolae mediated endocytosis (Table 3). In addition, the possible involvement of $Ca^{2+}$ entry pathways was investigated by employing Nifedipine, a blocker of L-type calcium channel and $Cd^{2+}$, a competitive inhibitor of $Ca^2$. The inhibitor concentration (Table 3) was chosen in a preliminary study exploring the effect of a range of concentrations on cell viability.

Figure 17A:
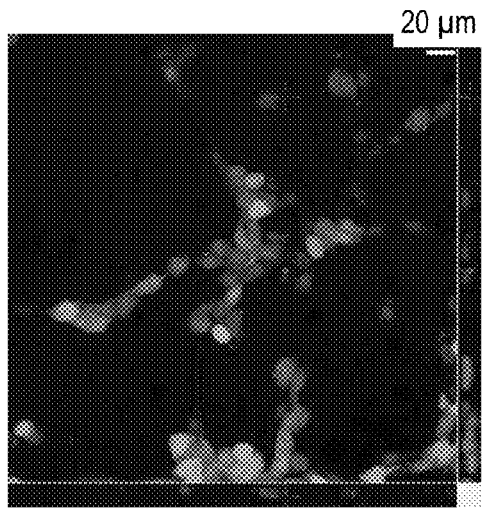
FIGS. 17A-17G show the effect of inhibitors on cellular uptake. Uptake of $Ca^{2+}$-siRNA (Cy3 labeled) binary complexes (A-F) and silencing in CT26 eGFP cells (G) in the presence of inhibitors for uptake pathways. A. Dynasore 50 µM. B. Pitstop2® 15 µM. C. Genistein 60 µM. D. $CdCl_2$ 50 nM. E. Nifedipine 20 µM. Green: CT26 cells; blue: nucleus; red: Cy3-labeled siRNA. F. Effect of inhibitors on total siRNA in cells transfected. MFI—mean fluorescence intensity (mean±STD, n=3). G. % eGFP silencing as detected by FACS. (Mean±STD, n=3). Each pair—left: after 24 hours, right: after 48 hours.
Figure 17B:
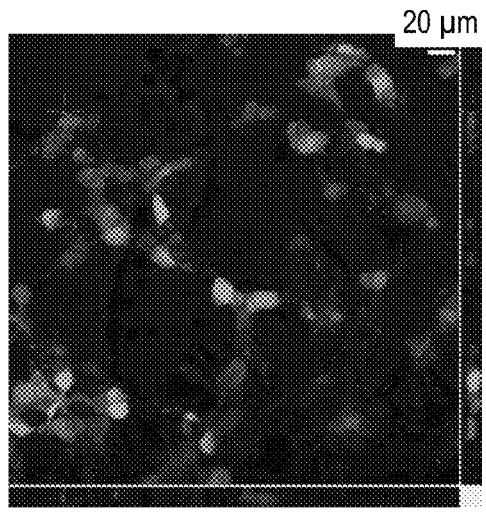
Figure 17C:
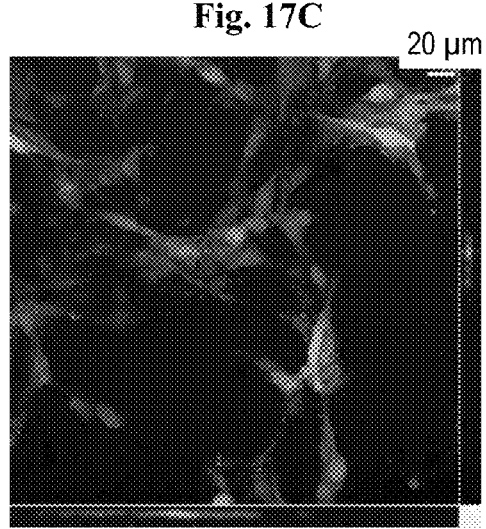
Figure 17D:
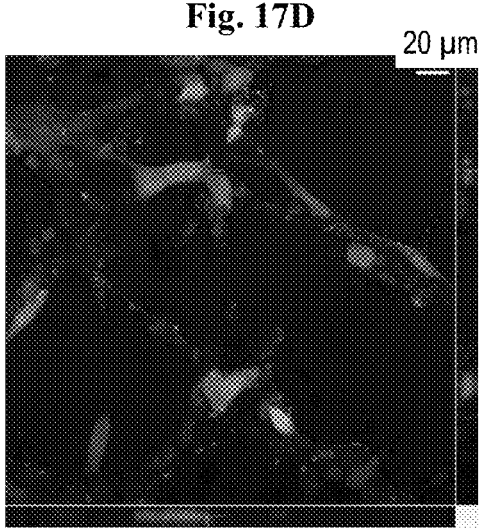
Figure 17E:
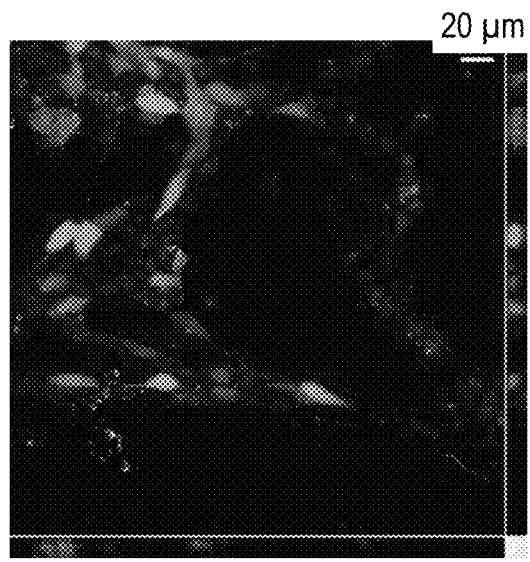

LSCM analysis revealed that Dynasore (FIG. 17A), Pitstop2® (FIG. 17B) and Genistein (FIG. 17C) all had an inhibitory effect on the entry of the $Ca^{2+}$-siRNA nanocomplexes, as judged by the accumulating fluorescent red particles on the cell membrane (the orange cross sign symbolizing the nanocomplex is lining with the membrane and not cytoplasm in the XZ and YZ planes). Pitstop2® showed the strongest inhibitory effect. By contrast, Nifedipine and $CdCl_2$, had no inhibitory effect on nanocomplex entry into the cell cytoplasm (as seen by the orange cross signs symbolizing the nanocomplexes lining with the cytoplasm in the XZ and YZ planes) (FIG. 17D,E).

Figure 17F:
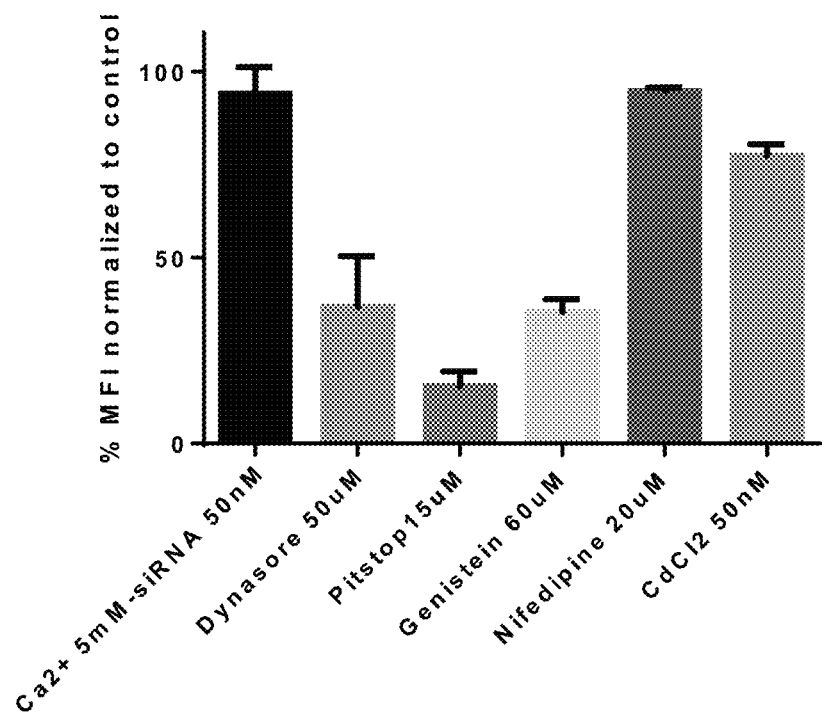

ImagestreamX analysis quantitatively confirmed that Dynasore, Pitstop2® and Genistein caused a significant decrease in the percentage of cells taking up the nanocomplexes, with Pitstop2® showing the most significant effect. $CdCl_2$ showed a slight decrease and Nifedipine did not demonstrate any difference compared to $Ca^{2+}$-siRNA nanocomplexes indicating the entry is not mediated by $Ca^{2+}$ channels. (FIG. 17F).

Figure 17G:
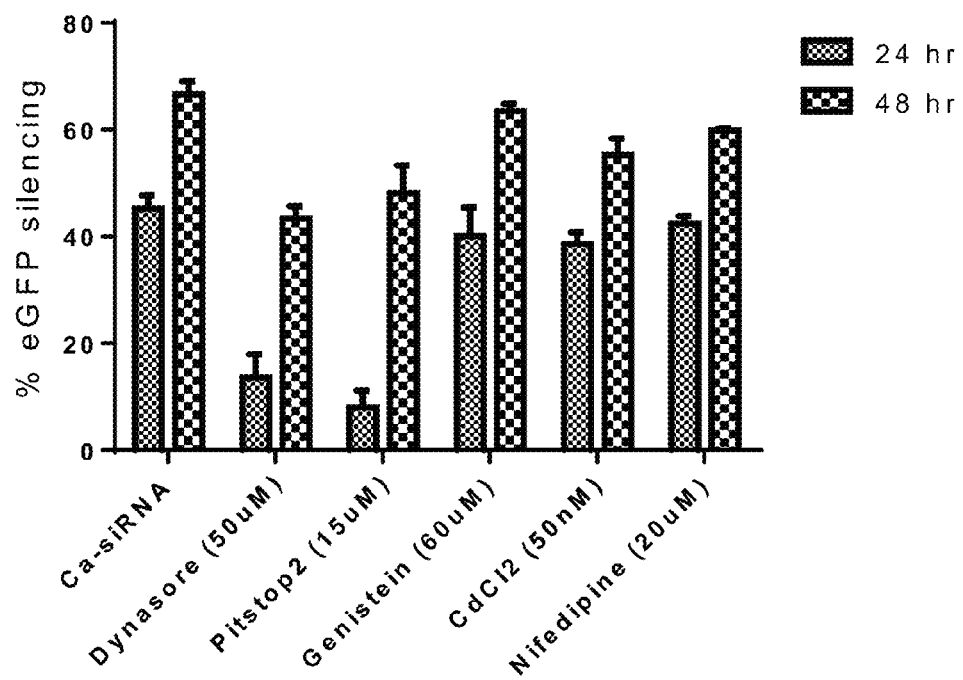

Silencing experiments confirmed that both Dynasore and PitStop2® significantly lowered silencing for 24 h. Surprisingly, Genistein did not inhibit silencing while Nifedipine and $CdCl_2$, as expected, did not affect silencing (FIG. 17G). However after 48 h the silencing was achieved in all inhibitors suggesting a limited effect due to the reversible effect of the inhibitors. Control of each inhibitor without the nano-complexes did not produce silencing (data not shown).

Example 16

Effect of Inhibitors on Endosomal Release

Figure 18A:
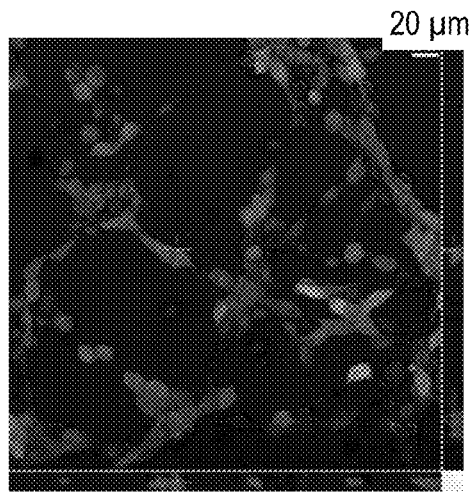
FIGS. 18A-18D show the effect of inhibitors on endosomal release. Uptake of Ca-siRNA (Cy3 labeled) binary complexes (A-B) and silencing of CT26 eGFP cells using inhibitors for endosomal release. A. Bafilomycin 75 nM. B. YM201636 2 µM. C. Effect of inhibitors on total siRNA in cells transfected (mean±STD, n=3). D. % eGFP silencing as detected by FACS. (Mean±STD, n=2). Each pair—left: after 24 hours, right: after 48 hours.
Figure 18B:
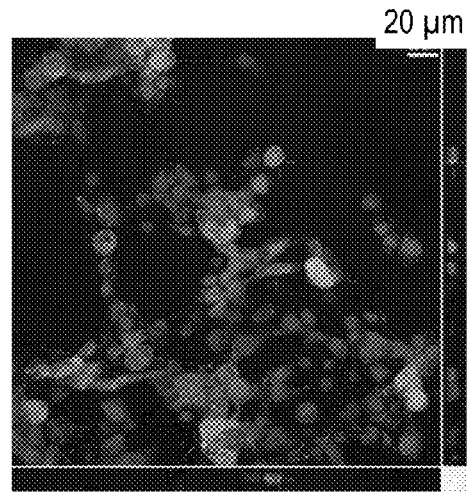
Figure 18C:
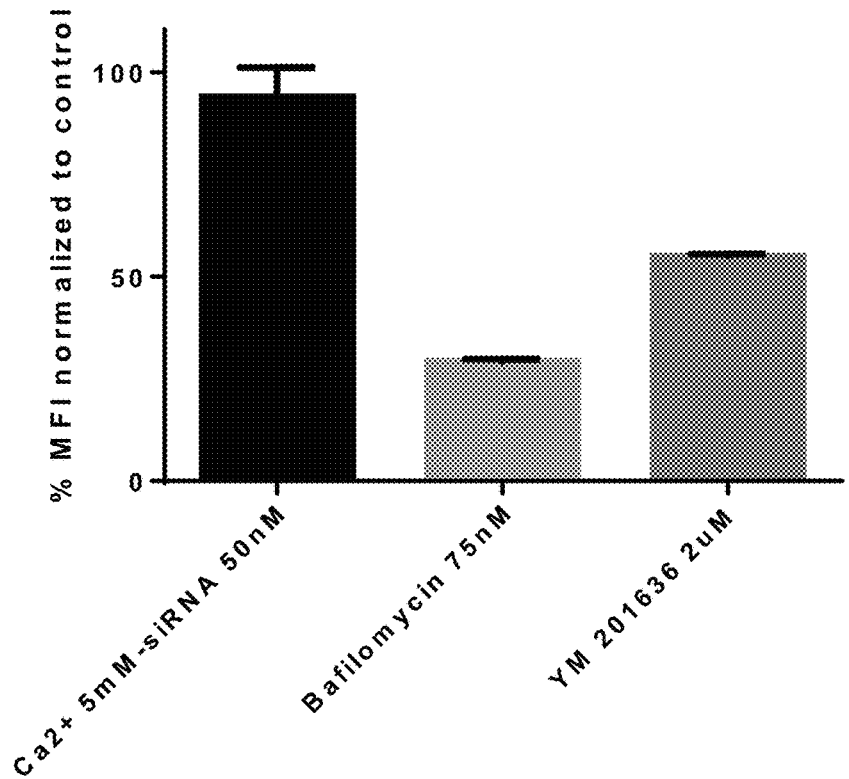
Figure 18D:
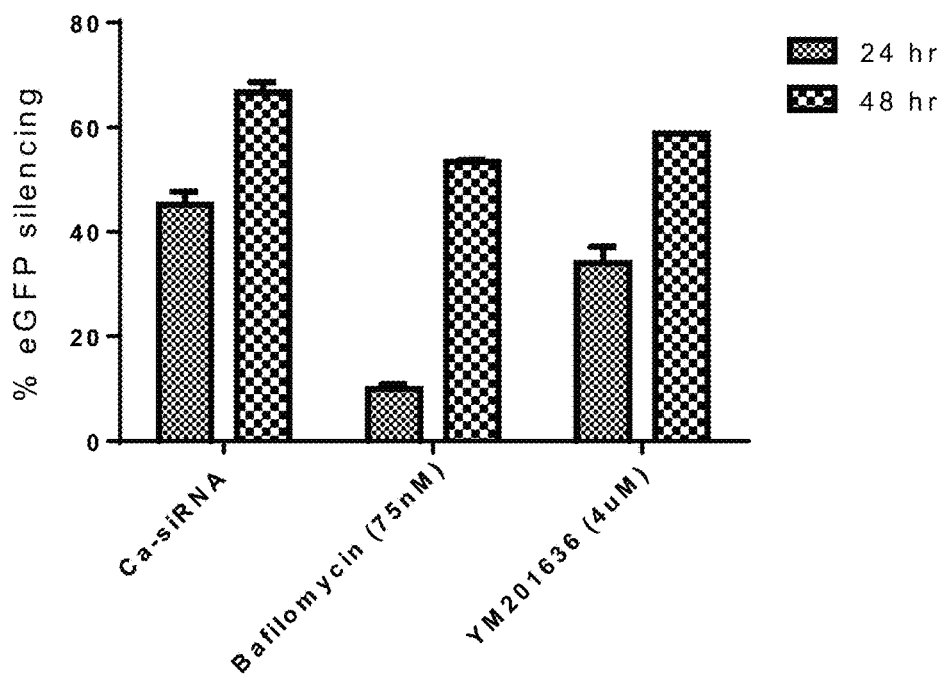

To elucidate particle endosomal escape, two inhibitors were employed: Bafilomycin A1, an ATPase inhibitor which blocks endosome acidification, and YM201636, a PIKfyve inhibitor, which blocks progression of endosomes from early to late endosome. LSCM analysis demonstrated a lesser amount of internalized $Ca^{2+}$-siRNA nanocomplexes in the Bafilomycin-treated cells (as seen by the orange cross in the XZ and YZ planes, FIG. 18A). YM201636, however, did not show inhibitory effect on uptake of the nanocomplexes (FIG. 18B). Quantitative analysis using ImagestreamX showed that Bafilomycin causes a significant decrease in the extent of cell uptake of $Ca^{2+}$-siRNA nanocomplexes, while YM201636's effect was less substantial (FIG. 18C). FACS experiments showed that Bafilomycin caused a significant reduction in eGFP silencing after 24 h and slightly reduced silencing after 48 h, while YM201636 did not show a significant reduction in gene silencing after 24 or 48 h of treatment (FIG. 18D).

REFERENCES

Asselin C., and Blais M., Transcriptional Regulation of Acute Phase Protein Genes, 2011.

Amarzguioui M., Rossi J., Principles of Dicer Substrate (D-siRNA) Design and Function, in: S. Barik (Ed.) RNAi, Humana Press, 2008, pp. 3-10.

Bellare J. R., Davis H. T., Scriven L. E., and Talmon Y., Controlled environment vitrification system: an improved sample preparation technique, Journal of electron microscopy technique, 10 (1988) 87-111.

Borgstrom J., Piculell L., Viebke C., and Talmon Y., On the structure of aggregated kappa-carrageenan helices. A study by cryo-TEM, optical rotation and viscometry, International journal of biological macromolecules, 18 (1996) 223-229.

Brock M., Trenkmann M., Gay R. E., Gay S., Speich R., and Huber L. C., MicroRNA-18a enhances the interleukin-6-mediated production of the acute-phase proteins fibrinogen and haptoglobin in human hepatocytes, The Journal of biological chemistry, 286 (2011) 40142-40150.

Jones, C. H., Chen, C. K., Ravikrishnan, A., Rane, S. & Pfeifer, B. A., 2013, Overcoming Nonviral Gene Delivery Barriers: Perspective and Future. *Molecular pharmaceutic*, 10 (11), 4082-4098.

Kedmi, R., Ben-Arie, N. & Peer, D., 2010, The systemic toxicity of positively charged lipid nanoparticles and the role of Toll-like receptor 4 in immune activation. *Biomaterials* 31, 6867-6875.

Nerstedt A., and Johansson A., C. X. Andersson, E. Cansby, U. Smith, M. Mahlapuu, AMP-activated protein kinase inhibits IL-6-stimulated inflammatory response in human liver cells by suppressing phosphorylation of signal transducer and activator of transcription 3 (STAT3), Diabetologia, 53 (2010) 2406-2416.

Rose S., Behlke M., Synthetic Dicer-Substrate siRNAs as Triggers of RNA Interference, in: K. A. Howard (Ed.) RNA Interference from Biology to Therapeutics, Springer US, 2013, pp. 31-56.

Shim, M. S. & Kwon, Y. J., 2012, Stimuli-responsive polymers and nanomaterials for gene delivery and imaging applications. *Adv Drug Deliv Rev* 64, 1046-1059.

The invention claimed is:

1. An anionic polyplex in the form of a nanoparticle or a microparticle formed from a nucleic acid and an anionic polymer and further comprising a cation, wherein said anionic polyplex has a diameter of 50-200 nm as measured by dynamic light scatter (DLS) and the molecular weight of said alginate sulfate is between 30 and 200 kDa.

2. The anionic polyplex of claim 1, wherein said alginate sulfate comprises a targeting moiety.

3. The anionic polyplex of claim 1, wherein said cation is a divalent cation selected from the group consisting of $Ca^{2+}$, $Ba^{2+}$, $Mg^{2+}$ and $Mn^{2+}$.

4. The anionic polyplex of claim 3, wherein said divalent cation is $Ca^{2+}$.

5. The anionic polyplex of claim 1, which is an (alginate-sulfate)-$Ca^{2+}$-siRNA polyplex.

6. The anionic polyplex of claim 1, wherein said nucleic acid is selected from the group consisting of siRNA, miRNA, mRNA and DNA.

7. The anionic polyplex of claim 6, wherein said nucleic acid is a siRNA.

8. The anionic polyplex of claim 1, wherein said nucleic acid is capable of silencing of a gene associated with a disease, disorder or condition selected from the group consisting of cancer, a metabolic, a neurodegenerative, a cardiovascular, and an infectious or inflammatory disease or disorder.

9. The anionic polyplex of claim 1, wherein the nucleic acid is RNA and the molar ratio between the alginate sulfate and the RNA is between 10:1 and 0.01:1.

10. The anionic polyplex of claim 9, wherein said molar ratio is about 6:1.

11. The anionic polyplex of claim 7, wherein the molar ratio between the alginate sulfate and the siRNA is about 6:1.

* * * * *

SEQUENCE LISTING

<160> NUMBER OF SEQ ID NOS: 18

<210> SEQ ID NO 1
<211> LENGTH: 19
<212> TYPE: RNA
<213> ORGANISM: Artificial Sequence
<220> FEATURE:
<223> OTHER INFORMATION: Nucleic acid

<400> SEQUENCE: 1
gccacaacgu cuauaucau                                          19

<210> SEQ ID NO 2
<211> LENGTH: 19
<212> TYPE: RNA
<213> ORGANISM: Artificial Sequence

```
<220> FEATURE:
<223> OTHER INFORMATION: nucleic acid

<400> SEQUENCE: 2
augauauaga cguuguggc                                          19

<210> SEQ ID NO 3
<211> LENGTH: 27
<212> TYPE: RNA
<213> ORGANISM: Artificial Sequence
<220> FEATURE:
<223> OTHER INFORMATION: nucleic acid

<400> SEQUENCE: 3
uccaguuucu uaauuguug acgggguc                                 27

<210> SEQ ID NO 4
<211> LENGTH: 25
<212> TYPE: RNA
<213> ORGANISM: Artificial Sequence
<220> FEATURE:
<223> OTHER INFORMATION: nucleic acid

<400> SEQUENCE: 4
cccgucaaca aauuaagaaa cugga                                   25

<210> SEQ ID NO 5
<211> LENGTH: 25
<212> TYPE: RNA
<213> ORGANISM: Artificial Sequence
<220> FEATURE:
<223> OTHER INFORMATION: nucleic acid

<400> SEQUENCE: 5
cguuaaucgc guauaauacg cguau                                   25

<210> SEQ ID NO 6
<211> LENGTH: 27
<212> TYPE: RNA
<213> ORGANISM: Artificial Sequence
<220> FEATURE:
<223> OTHER INFORMATION: nucleic acid

<400> SEQUENCE: 6
auacgcguau uauacgcgau uaacgac                                 27

<210> SEQ ID NO 7
<211> LENGTH: 27
<212> TYPE: RNA
<213> ORGANISM: Artificial Sequence
<220> FEATURE:
<223> OTHER INFORMATION: nucleic acid

<400> SEQUENCE: 7
uccuuccucu cuuucucucc cuuguga                                 27

<210> SEQ ID NO 8
<211> LENGTH: 27
<212> TYPE: RNA
<213> ORGANISM: Artificial Sequence
<220> FEATURE:
<223> OTHER INFORMATION: nucleic acid

<400> SEQUENCE: 8
ucacaaggga gagaaagaga ggaagga                                 27
```

<210> SEQ ID NO 9
<211> LENGTH: 20
<212> TYPE: DNA
<213> ORGANISM: Artificial Sequence
<220> FEATURE:
<223> OTHER INFORMATION: nucleic acid

<400> SEQUENCE: 9
aggagcgcac catcttcttc                                               20

<210> SEQ ID NO 10
<211> LENGTH: 24
<212> TYPE: DNA
<213> ORGANISM: Artificial Sequence
<220> FEATURE:
<223> OTHER INFORMATION: nucleic acid

<400> SEQUENCE: 10
atgatataga cgttgtggct gttg                                          24

<210> SEQ ID NO 11
<211> LENGTH: 20
<212> TYPE: DNA
<213> ORGANISM: Artificial Sequence
<220> FEATURE:
<223> OTHER INFORMATION: nucleic acid

<400> SEQUENCE: 11
cgactgtgga cagctctaat                                               20

<210> SEQ ID NO 12
<211> LENGTH: 20
<212> TYPE: DNA
<213> ORGANISM: Artificial Sequence
<220> FEATURE:
<223> OTHER INFORMATION: nucleic acid

<400> SEQUENCE: 12
cctgagctac agaaggaatg                                               20

<210> SEQ ID NO 13
<211> LENGTH: 18
<212> TYPE: DNA
<213> ORGANISM: Artificial Sequence
<220> FEATURE:
<223> OTHER INFORMATION: nucleic acid

<400> SEQUENCE: 13
ctgcagaagt gatcagcg                                                 18

<210> SEQ ID NO 14
<211> LENGTH: 18
<212> TYPE: DNA
<213> ORGANISM: Artificial Sequence
<220> FEATURE:
<223> OTHER INFORMATION: nucleic acid

<400> SEQUENCE: 14
attgtgtacc ctctcccc                                                 18

<210> SEQ ID NO 15
<211> LENGTH: 20
<212> TYPE: DNA
<213> ORGANISM: Artificial Sequence
<220> FEATURE:
<223> OTHER INFORMATION: nucleic acid

```
<400> SEQUENCE: 15
tagccagctt accaggatgg                                              20

<210> SEQ ID NO 16
<211> LENGTH: 23
<212> TYPE: DNA
<213> ORGANISM: Artificial Sequence
<220> FEATURE:
<223> OTHER INFORMATION: nucleic acid

<400> SEQUENCE: 16
ggctgttcct ctgtatttgt tca                                          23

<210> SEQ ID NO 17
<211> LENGTH: 26
<212> TYPE: DNA
<213> ORGANISM: Artificial Sequence
<220> FEATURE:
<223> OTHER INFORMATION: nucleic acid

<400> SEQUENCE: 17
atagcacagc ctggatagca acgtac                                       26

<210> SEQ ID NO 18
<211> LENGTH: 25
<212> TYPE: DNA
<213> ORGANISM: Artificial Sequence
<220> FEATURE:
<223> OTHER INFORMATION: nucleic acid

<400> SEQUENCE: 18
caccttctac aatgagctgc gtgtg                                        25
```